US006415234B1

(12) United States Patent
Andre et al.

(10) Patent No.: US 6,415,234 B1
(45) Date of Patent: Jul. 2, 2002

(54) DESIGNING INHIBITORS FOR GLYCOSYLTRANSFERASES

(75) Inventors: Isabelle Andre; Igor Tvaroska; Jeremy Carver, all of Toronto (CA)

(73) Assignee: Glyco Design Inc., Toronto ( * ) Notice: Subject to any disclaimer, the term of this patent is extended or adjusted under 35 U.S.C. 154(b) by 0 days.

(21) Appl. No.: 09/365,024

(22) Filed: Aug. 2, 1999

Related U.S. Application Data
(60) Provisional application No. 60/095,040, filed on Aug. 3, 1998.

(51) Int. Cl.[7] .......................... G01N 31/00; C07H 1/00

(52) U.S. Cl. ........................ 702/27; 536/18.5; 536/127

(58) Field of Search ............................... 536/18.5, 127; 702/27

(56) References Cited

PUBLICATIONS

Varki, A. *Glycobiology* 1993, 3, 97–130.
Sinnott, M.L. *Chem. Rev.* 1990, 90, 1171–1202.
Legler, G. *Carbohydr. Res.* 1993, 250, vii–xx.
Withers, S. G.; Aebersold, R. *Protein Sci.* 1995, 4, 361–372.
Khatra, B. S.; Herries, D.G.; Brew, K. *Eur. J. Biochem.* 1974, 44, 537–560.
Tsopaknakis, A. D.; Herries, D. G. *Eur. J. Biochem.* 1978, 83, 179–188.
Bendiak, B.; H. Schachter, H. *J. Biol. Chem.* 1987, 262, 5784–5790.
Nishikawa, Y.; Pegg, W.; Paulsen, H. *J. Biol. Chem.* 1988, 263, 8270–8281.
Kim, S. C.; Singh, A. N.; Raushel, F. M. *J. Biol. Chem.* 1988, 263, 10151–10154.
Kim, S. C.; Singh, A. N.; Raushel, F. M. *Arch. Biochem. Biophys.* 1988, 267, 54–58.
Kearns, A. E.; Campbell, S. C.; Westley, J.; Schwartz, N. B. *Biochemistry* 1991, 30, 7477–7483.
Ats, S.–C.; Lehmann, J.; Petry, S. *Carbohydr. Res.* 1992, 233, 125–139.
Nakazawa, K.; Furukawa, K.; Narimatsu, K.; Kobata, A. *J. Biochem.* 1993, 113, 747–753.
Yin, H.; Bennett, G.; Jones, J. P. *Chem. Biol. Interactions* 1994, 90, 47–58.
Breuer, W.; Bause, E. *Eur. J. Biochem.* 1995, 228, 689–696.
Strokopytov, B.; Penninga, D.; Rozeboom, H. J.; Kalk, K. H.; Dijkstra, B. W. *Biochemistry* 1995, 34, 2234–2240.
Qiao, L.; Murray, B. W.; Shimazaki, M.; Schultz, J.; Wong, C. *J. Am. Chem. Soc.* 1996, 118, 7653–7662.
Beyer, T. A.; Sadler, J. E.; Rearick, J. I.; Paulson, J. C.; Hill, R. L. *Adv. Enzymol.* 1981, 52, 23–175.
Kleene, R. et al., *Biochim. Biophys. Acta.* 1993, 1154, 283–325.
Becke, A. D. *J. Chem. Phys.* 1993, 98, 5648–5652.
Tvaroska, I.; Bleha, T. *Chem. Pap.* 1985, 39, 805–847.

Tvaroska, I. In *Theoretical Chemistry of Biological Systems*; Naray–Szabo G., Ed.; Elsevier: Amsterdam, 1986, pp 283–348.
Gorenstein, D. G. *Chem. Rev.* 1987, 87, 1047–177.
Sinnott, M. L. *Adv. Phys. Org. Chem.* 1988, 24, 113–204.
Tvaroska, I.; Bleha, T. *Adv. Carbohydr. Chem. Biochem.* 1989, 47, 45–123.
Juaristi, E.; Cuevas, G. *Tetrahedron* 1992, 48, 5019–5087.
Florian, J.; Baumruk, V.; Strajbl, M.; Bednarova, L.; Stepanek, J. *J. Phys. Chem.* 1996, 100, 1559–1568.
Schneider, B.; Kabelac, M.; Hobza, P. *J. Am. Chem. Soc.* 1996, 118, 12207–12217.
Tvaroska, I.; Carver, J. P. *J. Molec. Struct., THEOCHEM,* 1997, 395–396, 1–15.
Tvaroska, I.; Carver, J. P. *J. Phys. Chem.* 1994, 98, 6452–6458.
Tvaroska, I.; Carver, J. P. *J. Phys. Chem.* 1994, 98, 9477–9485.
Tvaroska, I.; Carver, J. P. *J. Phys. Chem.* 1995, 99, 6234–6241.
Tvaroska, I.; Carver, J. P. *J. Phys. Chem.* 1996, 100, 11305–11313.
Tvaroska, I.; Carver, J. P. *J. Phys. Chem. B* 1997, 101, 2992–2999.
Warshel, A., Florian J., *Proc. Natl. Acad. Sci. U.S.A.*, 1998, 95, 5950–5955.
Tvaroska, I.; Vaclavik, L. *Carbohydr. Res.* 1987, 160, 137–149.
Dowd, M. K.; Reilly, P. J.; French, A. D. *J. Comput. Chem.* 1992, 13, 102–114.
J.J. Pavelites, J. Gao, P.A. Bash and A.D. Mackerell, Jr., J. Comput. Chem. 18 (1997) 221–239.
Murphy, R. B.; Beachy, M. D.; Friesner, R. A.; Ringnalda, M. N. *J. Chem. Phys.* 1995, 103, 1481–14.
Tannor, D. J.; Marten, B.; Murphy, R.; Friesner, R. A.; Sitkoff, D.; Nicholls, A.; Ringnalda, M.; Goddard III, W. A.; Honig, B. *J. Am. Chem. Soc.* 1994, 116, 11875–11882.
Steiner, T.; Saenger, W. *J. Am. Chem. Soc.* 1992, 114, 10146–10154.
Aakeroy, C. B.; Seddon, K. R. *Chem. Soc. Rev.* 1993, 397–407.
Lemieux, R. U.; Morgan, A. R. *Can. J. Chem.* 1965, 43, 2205–2213.
Jones, P. G.; Kirby, A. J. *J. Am. Chem. Soc.* 1984, 106, 6207–6212.
Bürgi, H.–B.; Dubler–Steudle, K. C. *J. Am. Chem. Soc.* 1988, 110, 7291–7299.

(List continued on next page.)

Primary Examiner—Elli Peselev
(74) *Attorney, Agent, or Firm*—Millen, White, Zelano & Branigan, P.C.

(57) ABSTRACT

The invention relates to the design of inhibitors for glycosyltransferases, and in particular to computer-implemented methods for designing the inhibitors. The invention also relates to compositions and treatments using the inhibitors.

16 Claims, 9 Drawing Sheets

OTHER PUBLICATIONS

J.W. Dennis, S. Laferte, C. Waghorne, M.L. Breitman and R.S. Kerbel, Science,, 236 (1987) 582–585.

B. Ma, C. Meredith and H.F. Schaefer, III, J. Phys. Chem., 98 (1994) 8216–8223.

B. Ma, C. Meredith and H.F. Schaefer, III, J. Phys. Chem., 99 (1995) 3815–3822.

M.E. Colvin, E. Evleth and Y. Akacem, J. Am. Chem. Soc., 117 (1995) 4357–4362.

H. Saint–Martin, L.E. Ruiz–Vicent, A. Ramirez–Solis and I. Ortega–Blake, J. Am. Chem. Soc., 118 (1996) 12167–12273.

G.R. Desiraju, Acc. Chem. Res., 24 (1991) 290–296.

S.E. Barrows, F.J. Dulles, C.J. Cramer, A.D. French, and D.G. Truhlar, Carbohydr. Res., 276 (1995) 219–251.

J. Andzelm, J. Baker, A. Scheiner, and M. Wrinn, Int. J. Quantum Chem. 56 (1995) 733–746.

Deerfield, I., D. W.; Lapadat, M. A.; Spremulli, L. L.; Hiskey, R. G.; Pedersen, L. G. *J. Biomol. Struct. & Dynamics* 1989, 6, 1077–1091.

Krauss, M., Stevens, W.J.J. Am. Chem Soc. 1990, 112, 1460–1466.

(1)

(2)

(1)

(2)

GmGTmAmG (D)

GTGAG (G)

GGmGTG (B)

GmGmATG (C)
Two water molecules (Nwaters = 2)
Three water molecules (Nwaters = 3)

GGGAG (F)
Four water molecules (Nwaters = 4)

GmAGmAmG (A)
GGAGG (E)

DESIGNING INHIBITORS FOR GLYCOSYLTRANSFERASES

This application claims the benefit of the filing date of U.S. Provisional Application Ser. No. 60/095,040, filed Aug. 3, 1998.

FIELD OF THE INVENTION

The invention relates to the design of carbohydrate processing inhibitors for glycosyltransferases based on the conformational properties of the sugar phosphate linkage and/or phosphate linkages in nucleotide-sugar donors for the glycosyltransferases.

BACKGROUND OF THE INVENTION

The oligosaccharide chains of N— and O-linked glycoproteins play a crucial role in a number of biological processes [1,2]. Their biosynthesis and degradation pathways are therefore areas of significant interest for biology, medicine, and biotechnology. The assembly of the various types of oligosaccharides involves several glycosidases and glycosyltransferases. In comparison with glycosidases, the mechanisms of which have been characterized in some detail [3-5] the catalytic mechanism of glycosyltransferases have not yet been investigated in detail, though some kinetic studies have been reported [6-18].

Glycosyltransferases are a diverse group of enzymes that catalyze the transfer of a single monosaccharide unit from a donor to the hydroxyl group of an acceptor saccharide. [19, 20] The acceptor can be either a free saccharide, glycoprotein, glycolipid, or polysaccharide. The donor can be a nucleotide-sugar, dolichol-phosphate-sugar or dolichol-pyrophosphate-oligosaccharide. Glycosyltransferases show a precise specificity for both the acceptor and sugar donor and generally require the presence of a metal cofactor, usually a divalent cation like manganese.

The knowledge of the structure of nucleotide-sugars is prerequisite for understanding the catalytic mechanism of glycosyltransferases and for developing inhibitors for these enzymes. The 3-D structure of nucleotide-sugars is determined to some extent by the conformation adopted by the phosphate linkage. However, despite the importance of the conformation adopted by the diphosphate linkages on the overall shape of nucleotide-sugars, the structure and the conformational properties of such linkage remains somewhat unspecified.

Few calculations have been performed on the diphosphate linkage. The structure of the lowest energy conformers of pyrophosphoric acid, its anions and alkali salts were studied to model the hydrolysis of pyrophosphate [2-5]. The presence of hydroxyl groups in pyrophosphates stabilizes their lowest energy conformers by intramolecular hydrogen bonds. However, such stabilizing interactions are not possible in nucleotide-sugars and the diphosphate linkage in nucleotide-sugars should exhibit a different conformational behavior.

SUMMARY OF THE INVENTION

The invention relates to the design of carbohydrate processing inhibitors for glycosyltransferases based on the conformational properties of the sugar-phosphate linkage and/or phosphate linkage in sugar nucleotide donors for the glycosyltransferases. The method permits the identification early in the drug development cycle of compounds which have advantageous properties.

In particular, the present inventors studied the conformational properties of the sugar-phosphate linkage with ab initio methods using the 2-O-methylphosphono-tetrahydropyran anion (1 in FIG. 1) and sodium 2-O-methylphosphono-tetrahydropyran (2 in FIG. 1) as models. The ab initio energy and geometry of the conformers around the C1—O1 and O—P bonds were determined at various levels of the self-consistent field (SCF) and adiabatic connection method of density functional theory. At all levels of ab initio theory, compound 1 preferred the trans to the gauche conformer around the C1—O1 bond. The presence of a sodium counter-ion completely reverses the relative energy of the conformers, such that in the ion-pair complex 2, the gauche conformer about the C1—O1 bond is favored The present inventors also carried out an ab initio study of the sugar-diphosphate linkage. Ab initio molecular orbital calculations of the 2-O-methyldiphosphono-tetrahydropyran dianion and the magnesium 2-O-methyldiphosphono-tetrahydropyran were used to model the conformational behaviour of the sugar-diphosphate linkage in sugar-nucleotides. The geometry and energy of conformers were calculated at different basis set levels, from 6-31G* to cc-pVTZ(-f)++, using the SCF, DFT/B3LYP, and LMP2 methods. The vibrational frequencies were calculated at the HF/6-31G* level and the zero-point energy, thermal and entropy corrections were evaluated. The results of conformational analyses show that interactions of the diphosphate linkage with the $Mg^{2+}$ cation alter the conformational preferences about the anomeric and the diphosphate linkages. These changes influence the overall 3D-shape adopted by nucleotide-sugars.

The differences in structures with the ions indicates an important function of the metal cofactor in the catalytic mechanism of glycosyltransferases. Complexation of the phosphate with the metal ion changes the conformation about the phosphate linkages and more specifically about one of the P—O bonds going from gauche to trans orientation; it changes the conformation of the sugar-phosphate linkage from trans to gauche orientation; it influences the overall 3D-shape adopted by molecules containing phosphate linkages such as sugar donors in order to adopt a correct shape for optimal enzymatic recognition and to achieve maximal catalytic efficiency; it activates the sugar-oxygen glycosidic bond by elongating the sugar-oxygen bond; and/or, it changes the charge distribution to make the protonation of the glycosidic oxygen more favored.

Therefore broadly stated, the present invention relates to a method for preparing a potential inhibitor of a glycosyltransferase comprising:

(a) combining a first sugar, a phosphate group, and a second sugar that is transferred by the glycosyltransferase to an acceptor for the glycosyltransferase, under conditions appropriate for formation of a bond between a carbon atom of the first sugar and a first oxygen atom of the phosphate group, and formation of a linkage between a carbon atom of the second sugar and a second oxygen atom of the phosphate group, wherein the orientation of the linkage is antiperiplanar, and preferably the distance between the carbon atom linked to the first sugar and the carbon atom linked to the second sugar is in the range 3.7 Å to 4.2 Å;

(b) combining a first sugar, a phosphate group, an ion, and a second sugar that is transferred by the glycosyltransferase to an acceptor for the glycosyltransferase, under conditions appropriate for formation of a bond between a carbon atom of the first sugar and a first oxygen atom of the phosphate group, a linkage between a carbon atom of the second sugar and a second oxygen atom of the phosphate group, and an electrostatic interaction between free oxygen atoms of the phosphate group and the ion, and wherein the orientation of the linkage is synclinal, and, preferably the distance between the carbon atom linked to the first sugar and the carbon atom linked to the second sugar is in the range 3.7 Å to 4.5 Å;

(c) combining a first sugar, a diphosphate group, and a second sugar that is transferred by the glycosyltransferase to an acceptor for the glycosyltransferase, under conditions appropriate for formation of a bond between a carbon atom of the first sugar and an oxygen atom of a first phosphate of the diphosphate group, and formation of a linkage between a carbon atom of the second sugar and an oxygen atom of a second phosphate of the diphosphate group, wherein the orientation of the linkage is antiperiplanar, phosphorous-oxygen bonds linking the first phosphate to the second phosphate of the diphosphate group are in a synclinal or anticlinal orientation, and synclinal orientation, respectively, or symmetrically related orientation, and preferably the distance between the carbon atom linked to the first sugar and the carbon atom linked to the second sugar is in the range 4.9 Å to 5.3 Å; or (d) combining a first sugar, a diphosphate group, an ion, and a second sugar that is transferred by the glycosyltransferase to an acceptor for the glycosyltransferase, under conditions appropriate for formation of a bond between a carbon atom of the first sugar and an oxygen atom of a first phosphate of the diphosphate group, a linkage between a carbon atom of the second sugar and an oxygen atom of a second phosphate of the diphosphate group, and an electrostatic interaction between two or more, preferably three, oxygen atoms of the diphosphate group and the ion, and wherein the orientation of the linkage is synclinal, phosphorous-oxygen bonds linking the first phosphate to the second phosphate of the diphosphate group are in antiperiplanar or -anticlinal orientation, and synclinal orientation, respectively, or symmetrically related orientations, and preferably the distance between the carbon atom linked to the first sugar and the carbon atom linked to the second sugar is in the range 5.1 Å to 5.8 Å.

The method of the invention may be a computer-implemented method for designing potential inhibitors of a glycosyltransferase. The method may comprise one of the following:

A. designing a nucleotide-sugar with a monophosphate linkage by (a) selecting a molecule comprising a first sugar, a phosphate group, and a second sugar that is transferred by the glycosyltransferase to an acceptor for the glycosyltransferase, wherein there is a bond between a carbon atom of the first sugar and a first oxygen atom of the phosphate group, and a linkage between a carbon atom of the second sugar and a second oxygen atom of the phosphate group, (b) optimizing the conformation of the molecule using ab initio quantum chemistry methods so that the orientation of the linkage is antiperiplanar, and preferably the distance between the carbon atom linked to the first sugar and the carbon atom linked to the second sugar is in the range 3.7 Å to 4.2 Å;

B. designing a nucleotide-sugar with a monophosphate linkage and having an electrostatic interaction between free oxygen atoms of the monophosphate and an ion by (a) selecting a molecule comprising a first sugar, a phosphate group, an ion, and a second sugar that is transferred by the glycosyltransferase to an acceptor for the glycosyltransferase, wherein there is a bond between a carbon atom of the first sugar and a first oxygen atom of the phosphate group, a linkage between a carbon atom of the second sugar and a second oxygen atom of the phosphate group, and an electrostatic interaction between free oxygen atoms of the phosphate group and the ion, (b) optimizing the conformation of the molecule using ab initio quantum chemistry methods so that the orientation of the linkage is synclinal, and, preferably the distance between the carbon atom linked to the first sugar and the carbon atom linked to the second sugar is in the range 3.7 Å to 4.5 Å;

C. designing a nucleotide-sugar with a diphosphate linkage by (a) selecting a molecule comprising a first sugar, a diphosphate group, and a second sugar that is transferred by the glycosyltransferase to an acceptor for the glycosyltransferase, and wherein there is a bond between a carbon atom of the first sugar and an oxygen atom of a first phosphate of the diphosphate group, and a linkage between a carbon atom of the second sugar and an oxygen atom of a second phosphate of the diphosphate group, and (b) optimizing the conformation of the molecule using ab initio quantum chemistry methods so that the orientation of the linkage is antiperiplanar, phosphorous-oxygen bonds linking the first phosphate to the second phosphate of the diphosphate group are in a synclinal or anticlinal orientation, and synclinal orientation, respectively, or symmetrically related orientations; and preferably the distance between the carbon atom linked to the first sugar and the carbon atom linked to the second sugar is in the range 4.9 Å to 5.3 Å; or D. designing a nucleotide-sugar with a diphosphate linkage and having an electrostatic interaction between free oxygen atoms of the diphosphate and an ion by (a) selecting a molecule comprising a first sugar, a diphosphate group, an ion, and a second sugar that is transferred by the glycosyltransferase to an acceptor for the glycosyltransferase, wherein there is a bond between a carbon atom of the first sugar and an oxygen atom of a first phosphate of the diphosphate group, a linkage between a carbon atom of the second sugar and an oxygen atom of a second phosphate of the diphosphate group, and an electrostatic interaction between two or more, preferably three, free oxygen atoms of the diphosphate group and the ion, (b) optimizing the conformation of the molecule using ab initio quantum chemistry methods so that the orientation of the linkage is synclinal, phosphorous-oxygen bonds linking the first phosphate to the second phosphate of the diphosphate group are in antiperiplanar or -anticlinal orientation, and synclinal orientation, respectively, or symmetrically related orientations, and preferably the distance between the carbon atom linked to the first sugar and the carbon atom linked to the second sugar is in the range 5.1 Å to 5.8 Å.

The ab initio calculations may be carried out using commercially available ab initio computer programs (e.g. Gaussian, Gaussian, Inc. Pittsburgh, Pa., Jaguar, Schrodinger, Inc. Portland, Oreg., Turbomole 95.0 program, San Diego: Biosym/MSI, 1995) using standard basis sets, and optimization of the geometry may be performed at the SCF level with the 6-31G* basis set.

The invention also contemplates inhibitors obtained using the methods of the invention. In an embodiment a potential inhibitor of a glycosyltransferase is provided comprising:

(a) a first sugar, a phosphate group, and a second sugar that is transferred by the glycosyltransferase to an acceptor for the glycosyltransferase, wherein there is a bond between a carbon atom of the first sugar and a first oxygen atom of the phosphate group, and a linkage between a carbon atom of the second sugar and a second oxygen atom of the phosphate group, wherein the orientation of the linkage is antiperiplanar, and preferably the distance between the carbon atom linked to the first sugar and the carbon atom linked to the second sugar is in the range 3.7 Å to 4.2 Å;

(b) a first sugar, a phosphate group, an ion, and a second sugar that is transferred by the glycosyltransferase to an acceptor for the glycosyltransferase, wherein there is a bond between a carbon atom of the first sugar and a first oxygen atom of the phosphate group, a linkage between a carbon atom of the second sugar and a second oxygen atom of the phosphate group, and an electrostatic interaction between free oxygen atoms of the phosphate and the ion, and wherein the orientation of the linkage is synclinal, and, preferably the distance between the carbon atom linked to the first sugar and the carbon atom linked to the second sugar is in the range 3.7 Å to 4.5 Å;

(c) a first sugar, a diphosphate group, and a second sugar that is transferred by the glycosyltransferase to an acceptor for the glycosyltransferase, and wherein there is a bond between a carbon atom of the first sugar and an oxygen atom of a first phosphate of the diphosphate group, and a linkage between a carbon atom of the second sugar and an oxygen atom of a second phosphate of the diphosphate group, and wherein the orientation of the linkage is antiperiplanar, phosphorous-oxygen bonds linking the first phosphate to the second phosphate of the diphosphate group are in a synclinal or anticlinal orientation; and synclinal orientation, respectively, or symmetrically related orientations, and preferably the distance between the carbon atom linked to the first sugar and the carbon atom linked to the second sugar is in the range 4.9 Å to 5.3 Å; or (d) a first sugar, a diphosphate group, an ion, and a second sugar that is transferred by the glycosyltransferase to an acceptor for the glycosyltransferase, wherein there is a bond between a carbon atom of the first sugar and an oxygen atom of a first phosphate of the diphosphate group, a linkage between a carbon atom of the second sugar and an oxygen atom of a second phosphate of the diphosphate group, and an electrostatic interaction between two or more, preferably three, free oxygen atoms of the diphosphate group and the ion, wherein the orientation of the linkage is synclinal, phosphorous-oxygen bonds linking the first phosphate to the second phosphate of the diphosphate group are in -anticlinal or antipleriplanar orientation, and synclinal orientation, respectively, or symmetrically related orientations, and preferably the distance between the carbon atom linked to the first sugar and the carbon atom linked to the second sugar is in the range 5.1 Å to 5.8 Å.

In a specific embodiment of the invention a computer-implemented method is provided for designing a potential inhibitor of a glycosyltransferase comprising (a) selecting a molecule comprising a group of the formula I

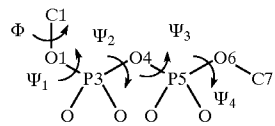

wherein C7 forms part of a first sugar; C1 forms part of a second sugar that is transferred by the glycosyltransferase to an acceptor for the glycosyltransferase; Φ is a dihedral angle defining rotation about C1—O1; $\Psi_1$ is a dihedral angle defining orientation about O1—P3; $\Psi_2$ is a dihedral angle defining orientation about P3—O4, $\Psi_3$ is a dihedral angle defining orientation about O4—P5, and (b) optimizing the conformation of the molecule so that Φ is in an antiperiplanar orientation, $\Psi_2$ is in a synclinal orientation or symmetrically related orientation, and $\Psi_3$ is in a synclinal or anticlinal orientation or a symmetrically related orientation. In a more preferred embodiment $\Psi_2$ is in a synclinal or -synclinal orientation and $\Psi_3$ is in a anticlinal or -anticlinal orientation. Most preferably Φ is between about 1000° and 170° or symmetrically related orientations, $\Psi_2$ is between about 60° and 120° or symmetrically related orientations, and $\Psi_3$ is between about −50° and −130° or symmetrically related orientations.

In an additional specific embodiment of the invention a computer-implemented method is provided for designing a potential inhibitor of a glycosyltransferase comprising (a) selecting a molecule comprising a group of the formula I and an ion

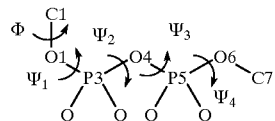

wherein C7 forms part of a first sugar; C1 forms part of a second sugar that is transferred by the glycosyltransferase to an acceptor for the glycosyltransferase; Φ is a dihedral angle defining rotation about C1—O1; $\Psi_1$ is a dihedral angle defining orientation about O1—P3; $\Psi_2$ is a dihedral angle defining orientation about P3—O4, and T3 is a dihedral angle defining orientation about O4—P5, and (b) optimizing the conformation of the molecule so that there is an electrostatic interaction between two or more, preferably three, free oxygen atoms of the molecule of the formula I and the ion, Φ is in a synclinal orientation, $\Psi_2$ is in a synclinal or a symmetrically related orientation, $\Psi_3$ is in an -anticlinal or antiperiplanar orientation or a symmetrically related orientation, more preferably $\Psi_2$ is in a synclinal orientation and $\Psi_3$ is in an -anticlinal orientation. In a most preferred embodiment Φ is between about 40° and 100° or symmetrically related orientations, $\Psi_2$ is between about 60° and 110° or symmetrically related orientations, and $\Psi_3$ is between about −90° and −100° (-ac) or 180±10° (ap) or symmetrically related orientations.

The invention contemplates a glycosyltransferase inhibitor comprising a group of the formula I

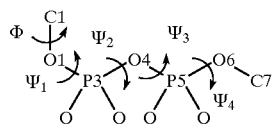

wherein C7 forms part of a first sugar; C1 forms part of a second sugar that is transferred by the glycosyltransferase to an acceptor for the glycosyltransferase; $\Phi$ is a dihedral angle defining rotation about C1—O2; $\Psi_1$ is a dihedral angle defining orientation about O1—P3; $\Psi_2$ is a dihedral angle defining orientation about P3—O4, and $\Psi_3$ is a dihedral angle defining orientation about O4—P5, and wherein $\Phi$ is in an antipleriplanar orientation, $\Psi_2$ is in a synclinal orientation or symmetrically related orientation, and $\Psi_3$ is in a synclinal or anticlinal orientation or a symmetrically related orientation. In a more preferred embodiment $\Psi_2$ is in a synclinal or -synclinal orientation and $\Psi_3$ is in a anticlinal or -anticlinal orientation. Most preferably, $\Phi$ is between about 100° and 170° or symmetrically related orientations, $\Psi_2$ is between about 60° and 120° or symmetrically related orientations, and $\Psi_3$ is between about −50° and −130°, or symmetrically related orientations.

The invention contemplates a glycosyltransferase inhibitor comprising a group of the formula I in combination with an ion

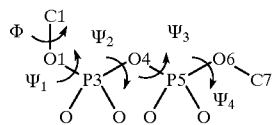

wherein C7 forms part of a first sugar, C1 forms part of a second sugar that is transferred by the glycosyltransferase to an acceptor for the glycosyltransferase, $\Phi$ is a dihedral angle defining rotation about C1—O1; $\Psi_1$ is a dihedral angle defining orientation about O1—P3; $\Psi_2$ is a dihedral angle defining orientation about P3O4, and $\Psi_3$ is a dihedral angle defining orientation about O4—P5, and wherein there is an electrostatic interaction between two or more, preferably three, free oxygen atoms of the molecule of the formula I and the ion, $\Phi$ is in a synclinal orientation, $\Psi_2$ is in a synclinal or a symmetrically related orientation, $\Psi_3$ is in an -anticlinal or antiperplanar orientation or a symmetrically related orientation, more preferably $\Psi_2$ is in a synclinal orientation and $\Psi_3$ is in an -anticlinal orientation. In a most preferred embodiment $\Phi$ is between about 40° and 100° or symmetrically related orientations, $\Psi_2$ is between about 60° and 110° or symmetrically related orientations, and $\Psi_3$ is between about −90° and −100° (−ac) or 180±10° (ap) or symmetrically related orientations.

Enzymes for which inhibitors may be prepared in accordance with the invention are glycosyltransferases including eukaryotic glycosyltransferases involved in the biosynthesis of glycoproteins, glycolipids, glycosylphosphatidylinositols and other complex glycoconjugates, and prokaryotic glycosyltransferases involved in the synthesis of carbohydrate structures of bacteria and viruses, including enzymes involved in LOS and lipopolysaccharide biosynthesis. Examples of glycosyltransferases are N-acetylglucosaminyltransferases, including N-acetylglucosaminyltransferases I through V, and β-1,3-galactosyl-O-glycosyl-glycoprotein β1,6-N-acetylgucosaminyl transferase (core 2 GlcNAc). Table 16 provides examples of eukaryotic glycosyltransferases, and their sugar nucleotide donors and acceptors. A "sugar nucleotide donor" refers to a nucleotide coupled to a selected sugar that is transferred by a glycosyltransferase to an acceptor. (The selected sugar is also referred to herein as "second sugar"). An "acceptor" refers to the part of a carbohydrate structure (e.g. glycoprotein, glycolipid) where the selected sugar is transferred by the glycosyltransferase.

The first sugar in an inhibitor of the invention may be a monosaccharide or disaccharide, preferably a monosaccharide. Examples of these sugars include galactose, glucose, mannose, ribose, fructose, deoxyribose, preferably ribose and deoxyribose. The first sugar may be modified for example, the hydroxyls may be blocked with acetonide, acylated, or alkylated or substituted with other groups such as halogen.

The first sugar may be part of a nucleoside namely guanosine, adenosine, thymidine, cytidine or uridine, preferably uridine. A heterocyclic amine base in a nucleoside may be modified. For example, when the base is uridine it may be modified at the C-5 position with groups including but not limited to alkyl or aryl with electron donating and electron withdrawing groups.

The second sugar is selected based on the type of glycosyltransferase to be inhibited, and it is typically D-GlcNAc (see Table 16).

The ion may be any counter-ion including sodium, lithium, potassium, calcium, magnesium, manganese, cobalt ions and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In a preferred embodiment of the invention an inhibitor is prepared comprising UDP-GlcNAc complexed with an ion, wherein the orientation of the linkage between the uridine deoxyribose phosphate and GlcNAc is synclinal, and the phosphorous-oxygen bonds linking the phosphates of the diphosphate ($\Psi_2$, $\Psi_3$) are in synclinal, and -anticlinal or antipleriplanar orientation, or a functional derivative thereof.

The term "functional derivative" is intended to include "variants" "analogs" or "chemical derivatives" of the inhibitors. The term "variant" is meant to refer to a molecule substantially similar in structure and function to an inhibitor or a part thereof. A molecule is "substantially similar" if it has a substantially similar structure or it possesses similar biological activity. The term "analog" refers to a molecule substantially similar in function to an inhibitor of the invention. The term "chemical derivative" describes a molecule that contains additional chemical moieties which are not normally a part of the base molecule, or one or more of the atoms is optionally replaced by another atom.

The inhibitors of the invention may be useful for the prevention, treatment and prophylaxis of tumor growth and metastasis of tumors; the prevention of tumor recurrence after surgery; the treatment of other anti-proliferative conditions such as viral infections; the stimulation of bone marrow cell proliferation, the treatment of immunocompromised patients, such as patients infected with HIV, or other viruses or infectious agents including bacteria and fungi; the prevention and treatment of diseases caused by bacterial pathogens having carbohydrate structures on their surface associated with virulence such as Neisseria, Haemophilus, E. coli, Bacillus, Salmonella, Campylobacter, Klebsiella, Pseudomonas, Streptococcus, Chlamydia, Borrelia, Coxiella, Helicobacter, and Mycobacterim species; or, the treatment of inflammatory disorders such as asthma, rheumatoid arthritis, inflammatory bowel disease, and atherosclerosis. The inhibitors may also be used in patients undergoing bone marrow transplants, and as hemorestorative or chemoprotective agents in patients with chemical or tumor-induced immune suppression.

The inhibitors may be converted using customary methods into pharmaceutical compositions. The pharmaceutical compositions contain the inhibitors either alone or together with other active substances. Such pharmaceutical compositions can be for oral, topical, rectal, parenteral, local, inhalant, or intracerebral use. They are therefore in solid or semisolid form, for example pills, tablets, creams, gelatin capsules, capsules, suppositories, soft gelatin capsules, liposomes (see for example, U.S. Pat. No. 5,376,452), gels, membranes, and tubelets. For parenteral and intracerebral uses, those forms for intramuscular or subcutaneous administration can be used, or forms for infusion or intravenous or intracerebral injection can be used, and can therefore be prepared as solutions of the inhibitors or as powders of the inhibitors to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays should be considered.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, the inhibitors in association with one or more pharmaceutically acceptable vehicles or diluents, and contained in buffered solutions with a suitable pH and iso-osmotic with the physiological fluids.

The inhibitors may be indicated as therapeutic agents either alone or in conjunction with other therapeutic agents or other forms of treatment (e.g. chemotherapy or radiotherapy). The inhibitors can be used to enhance activation of macrophages, T cells, and NK cells in the treatment of cancer and immunosuppressive diseases. By way of example, the inhibitors may be used in combination with anti-proliferative agents, antimicrobial agents, immuno-stimulatory agents, or anti-inflammatories. In particular, the inhibitors may be used in combination with anti-viral and/or anti-proliferative agents, such as Th1 cytokines including interleukin-2, interleukin-12, and interferon-γ, and nucleoside analogues such as AZT and 3TC. The inhibitors may be administered concurrently, separately, or sequentially with other therapeutic agents or therapies.

The compositions containing inhibitors can be administered for prophylactic and/or therapeutic treatments. In therapeutic applications, compositions are administered to a patient already suffering from a disease or condition as described above, in an amount sufficient to cure or at least alleviate the symptoms of the disease and its complications. An amount adequate to accomplish this is defined as a "therapeutically effective dose". Amounts effective for this use will depend on the severity of the disease, the weight and general state of the patient, the nature of the administration route, the nature of the formulation, and the time or interval at which it is administered.

In prophylactic applications, compositions containing inhibitors are administered to a patient susceptible to or otherwise at risk of a particular disease. Such an amount is defined to be a "prophylactically effective dose". In this use, the precise amounts depend on the patient's state of health and weight, the nature of the administration route, the nature of the formulation, and the time or interval at which it is administered.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF PREFERRED EMBODIMENTS

Figure 1:
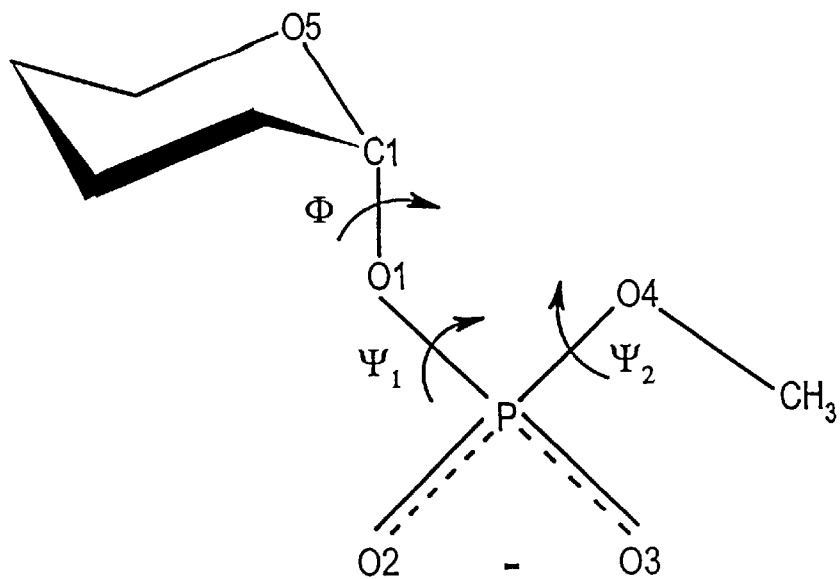
FIG. 1. Schematic representation of the 2-O-methylphosphono-tetrahydropyran anion (1) and sodium 2-O-methylphosphono-tetrahydropyran (2).
Figure 1:
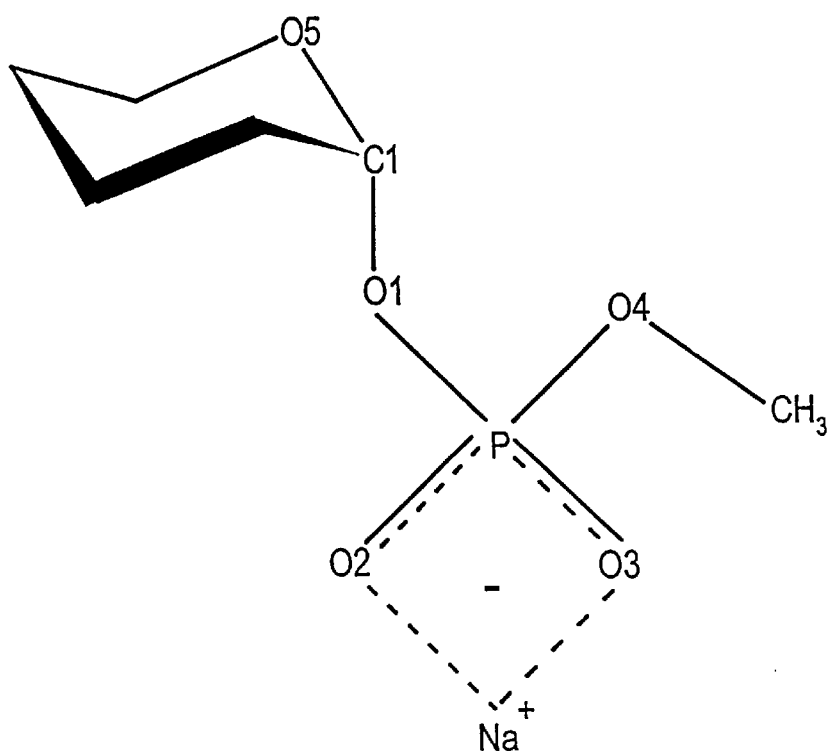

The following non-limiting examples illustrate the invention:

EXAMPLE 1 ab Initio Molecular Orbital Study of the Conformational Behavior of the Sugar-Phosphate Linkage Models and Computational Procedures The conformational behavior of the monophosphate functional group linked to the anomeric carbon in hexopyranosides has been studied with ab initio methods using the 2-O-methylphosphono-tetrahydropyran anion (1) and the sodium 2-O-methylphosphono-tetrahydropyran (2) as models. Structures of the compounds with axially oriented phosphate groups are illustrated in FIG. 1. These two species were chosen to represent different conformational features of the possible structures of the nucleotide-sugar donors in the enzyme-binding site. The numbering of atoms is in the carbohydrate nomenclature, where the anomeric carbon is denoted as C1, etc. The rotation about the anomeric C1—O1 linkage is described by the dihedral angle $\Phi[\Phi=\Phi(O5—C1—O1—P)]$, and the orientation of the phosphate group is described by dihedral angles $\Psi_1[\Psi_1=\Psi_1(C1—O1—P—O4)]$ and $\Psi_2[\Psi_2=\Psi_2(O1—P—O4—C)]$. Conformations of compounds 1 and 2 are then described using three torsion angles $\Phi$, $\Psi_1$, and $\Psi_2$. Three staggered orientations about the C1—O1, O1—P and P—O4 bonds are denoted as G (synclinal, gauche, 60°), T (antiperiplanar, trans, 180°), and mG (-synclinal, -gauche, −60°), respectively. In this notation, the description of the torsion angle $\Phi$ is stated first, then the torsion angles $\Psi_1$ and $\Psi_3$. In this way, e.g., GTmG means that the angles $\Phi$, $\Psi_1$, and $\Psi_2$ are approximately in synclinal (sc) or gauche (G), antiperiplanar (ap) or trans (T) and -synclinal (-sc) or -gauche (mG) conformations, respectively.

The ab initio calculations were carried out with the Turbomole 95.0 program [40] using standard basis sets. First, three possible staggered conformers around each of the C1—O1, O1—P and P—O4 bonds were assumed, giving altogether 27 different starting conformations for geometry optimization. The optimization of the geometry was performed at the SCF level with the 6-31G* basis set. The geometry was fully optimized using the gradient optimization routines of the program without any symmetry constraints. Next, single-point calculations were performed for each minimum using the triple-zeta basis set plus one set of polarization functions (tzp). It has been shown [32,35] that inclusion of electron correlation at the MP2/6-31G* level does not improve the results, therefore, electron correlation at this level was not included in the present study. Instead, a hybrid Hartree-Fock-density functional scheme, the adiabatic connection method [41] (ACM) of density functional theory [42] (DFT) was used for some conformers with standard 6-31G* and tzp basis sets. The extent of correlation effects at the ACM/6-31G* level on relative energies has been found to be smaller using the ACM method than that found with the MP2 method. [38] For all minima, the vibrational frequencies were calculated at the 6-31G* level, and the zero-point energy, thermal and entropy corrections were evaluated. For comparison, semi-empirical calculations were performed with the AMPAC/MOPAC module of the InsightII program [43] using the MNDO Hamiltonian. Molecular mechanics calculations were also done with the DISCOVER program [44] using the CVFF and AMBER force fields. Calculations were carried out on an Indigo 2 R10000 SGI computer.

Results and Discussion

A. 2-O-Methylphosphono-tetrahydropyran Anion (1)

The linkage of the phosphate group to the anomeric carbon results in three internal rotational degrees of freedom, associated with the C1—O1, O1—P, and P—O4 bonds. The assumption of three staggered conformers for each bond leads to 27 ($3^3$) conformers to be considered. However, the balance of electrostatic, steric, and lone pair intramolecular interactions is such that not all of these structures are minima. Indeed, from the 27 starting conformers only 16 minima were obtained. The results performed at various levels of computation are gathered in Tables 1–3 and in FIG. 2.

The ab initio potential energy profiles for rotation about the glycosidic C1—O1 linkage have been previously investigated in detail.[35] For 2-methoxytetrahydropyran with an axially oriented methoxy group, regardless of the method, only one deep well was predicted. The sc (G) orientation of the methyl group with respect to the ring oxygen ($\Phi=64.2°$) was found to be the most stable. The relative energy calculated for the ap (T) and -sc (mG) conformations at the 6-31G* level was 4.0 kcal/mol and 10.5 kcal/mol, respectively. Similarly, the preference for the sc over the ap conformation also has been observed for the C1—X bond in C—, N— and S-glycosyl compounds. [37] This feature has been attributed to the presence of the exo-anomeric effect.

Surprisingly, the results on the conformational properties about the C1—O1 bond for the 2-O-methylphosphono-tetrahydropyran anion are completely different from those found in the earlier studies discussed above. Calculations on 1 predicted three staggered conformers about the glycosidic C1—O1 bond. Each of these orientations consists of a set of conformers (Table 1) that differ in the conformation of the phosphate group. The order of stability of the orientations about the C1—O1 bond appears to be: first the ap (T), then the sc (G), and finally the -sc (MG) orientation. The lowest energy minimum is the TMGMG conformation which corresponds to the ap $\Phi=142.4°$) orientation about the glycosidic C1—O1 bond. The lowest energy conformer for the sc orientation is the GmGG ($\Phi=89.7°$) which has an energy at the 6-31G* level 1.4 kcal/mol above that of the TmGmG conformer. For the third orientation about the C1—O1 bond, the -sc, the lowest energy minimum mGmGmG ($\Phi=-100.6°$) has a relative energy of 6.66 kcal/mol. The preference for the ap orientation about the C1—O1 bond is thus clear, since from five conformers having this orientation, three of them (TmGmG, TTG, and TGG) have lower energy than the GmGG conformer, which is the lowest energy conformer for the sc orientation. It is noteworthy that values of the torsion angle $\Phi$ adopted by the individual minima lie in the range (61° to 90°) for the sc (G) conformers, (−57° to −101°) for the -sc (mG) conformers, and (142° to 170°) for the ap (T) conformers, respectively. The relatively large ranges of values for the $\Phi$ torsion angle indicate that the potential energy surface about the anomeric C1—O1 is nearly flat in these regions. This suggests that the negatively charged sugar phosphates exhibit considerably larger conformational flexibility about this bond compared to glycosides.

High level ab initio calculations of the dimethyl phosphate anion [32,33] gave ($\Psi_1$, $\Psi_2$=sc, sc) or its symmetrically equivalent conformer (-sc, -sc) as the most stable orientation. The relative energy of other conformers depended on the method of calculation but was found to be relatively small, usually within 3 kcal/mol. The (ap, sc) conformer is the next most favored, then the (sc, -sc) conformer having both methyl groups oriented on the same side of the molecule, and the (ap, ap) conformation is the least stable local minimum. The relative energies of the dimethyl phosphate anion conformers clearly illustrate the importance of the anomeric effect for the stereochemistry of the phosphate group. The phosphate group in the 2-O-methylphosphono-tetrahydropyran anion exhibits a similar degree of flexibility. However, due to the presence of the hexopyranose ring, the stable conformers are not symmetrically related as in the case of the dimethyl phosphate anion. Moreover, the stability of the conformers about the O1—P and P—O4 bonds depends on the conformation about the C1—O1 bond and is influenced by interactions with the six-member ring. Despite these structural differences, the anomeric effect remains a dominant factor in the stability of the phosphate group conformers of 1. This can be seen from the data in Table 1. For the ap (T) orientation about the C1—O1 bond, the TmGmG minimum that corresponds to the (-sc, -sc) conformation for the dimethyl phosphate anion has the lowest energy. The next lowest energy conformers are the TTG (ap, sc) and TGG (sc, sc) conformations, with energies approximately 0.9 kcal/mol and 1.3 kcal/mol higher than the TmGmG conformation. For the sc (G) orientation, the lowest energy conformer of the phosphate group is the GmGG (-sc, sc). The GTmG (ap, -sc) has approximately the same energy and the GTG (ap, sc) is 0.3 kcal/mol higher. For this orientation about the C1—O1 bond, surprisingly, the GGG (sc, sc) is the highest energy conformer (ΔE=4.1 kcal/mol). The relative energy of the GmGG conformer, with the phosphate group in the (-sc, sc) conformations is unexpectedly low. For the dimethyl phosphate anion, the relative energy [32,33] of the (-sc, sc) conformer is approximately 2.7 kcal/mol because of a steric C . . . C contact. For 1, steric interactions in the GmGG conformer are slightly relieved by a large deviation of the three torsion angles $\Phi$, $\Psi_1$, and $\Psi_2$ (90°, -90°, 98°) from the exact gauche orientation and by opening the C1—O1—P and P—O4—C bond angles (123°, 120°). Furthermore, an inspection of the spatial structure of the GmGG conformer revealed that the distance between the ring oxygen atom and one of the hydrogens of the methyl group is 2.63 Å and with the methyl carbon is 3.44 Å. This suggests that O5 . . . H—C hydrogen bond interactions might be responsible for this stabilization.

To estimate the influence of the basis set on the relative energy of conformers, single point calculations with the tzp//6-31G* basis set were carried out. A comparison of the relative energies (Table 1) reveals that enlargement of the basis set increases the relative energy of some conformers. This change is usually less than 0.5 kal/mol. Interestingly, the energy differences between the TmGmG and GmGG (GTmG) conformers increased from 1.4 kcal/mol to 1.78 kcal/mol (1.83 kcal/mol). A larger increase was found for the GGmG conformer, 3.63 vs. 4.42 kcal/mol. In this basis set, all ap conformers, except the TGT, have a lower energy compared to the other orientations. Thus, the predicted preference of the ap over the sc conformers about the C1—O1 bond is slightly larger at the higher level of calculation. To evaluate further the effect of the electron correlation and basis set, the relative energies of four relevant conformers (TmGmG, TTG, GmGG, and GTmG) of 1 were calculated using the 6-31-G* and tzp basis sets with the ACM method. The results of the ACM calculations are summarized in Table 2. The energies of the TTG, GmGG and GTmG conformers relative to the TmGmG conformer are 0.64 kcal/mol, 0.61 kcal/mol and 0.87 kcal/mol at the ACM/6-31G*//ACM/6-31G* level. Thus inclusion of electron correlation within the ACM DFT method at the 6-31G* level decreased the energy difference between the TmGmG and GMGG conformers about the C1—O1 bond from 1.4 kcal/mol to 0.61 kcal/mol. It can be seen from Table 2 that the ACM relative energies are basis set dependent and a further extension of the basis set increases the energy differences between conformers. Indeed, the ACM/tzp//ACM/6-31G* relative energies of the TTG, GmGG, and GTmG conformers changed to 0.91 kcal/mol, 1.00 kcal/mol, and 1.44 kcal/mol, respectively. The optimization of geometry with the ACM method at the tzp level only marginally altered these values to 0.92 kcal/mol, 1.02 kcal/mol and 1.38 kcal/mol. It is also noteworthy that the absolute energies of conformers at the ACM/tzp//ACM/tzp are very similar (within 0.5 kcal/mol) to those calculated at the ACM/tzp//ACM/6-3 1G* level. The relative energy values appear to be approaching those predicted by the 6-31G* basis set without taking into account electron correlation. The largest differences (~0.4 kcal/mol) between the 6-31G* and ACM/tzp methods have been found for the GmGG conformer. Similar behavior has been observed for dimethyl phosphate [32,33] and carbohydrate model compounds.[38] Therefore, the results indicate that, due to compensation of errors, calculations with the 6-31G* basis set at the HF level provides a reliable set of conformational energies and geometries for carbohydrate molecules.

To see what effect the zero-point energy, thermal energy and entropy might have on the calculated energy differences, the vibrational frequencies were calculated using the 6-31G* basis set. These were used to determine the zero-point energy, thermal energy and entropy of conformers. The results are given in Table 1. It can be seen that the conclusions regarding the stability conformers remain unchanged, supporting the preference of the ap over the sc orientation about the C1—O1 bond. The free energy differences are smaller than the energy differences and 9 conformers have their free energy within 1.5 kcal/mol. The TmGmG conformer remains the preferred species. Zero-point energies (130.95–131.09 kcal/mol) and thermal energies (138.16–138.33 kcal/mol) are very similar for all conformers. The entropy contribution (107.06–110.91 cal/mol.K) is responsible for the decrease in relative free energies.

The negatively charged phosphate group linked to anomeric carbon completely changes the conformational behavior of the anomeric C1—O1 bond in comparison to that observed in glycosides, where the gauche orientation of the aglycon carbon with respect to the ring oxygen is usually the dominant conformer due to the exo-anomeric effect. These unexpected results suggest that the influence of the exo-anomeric effect on the relative energy of conformers is not a decisive factor in negatively charged sugar phosphates. In other words, joining two groups, the acetal group (C5—O5—C1—O1—C) with the negatively charged phosphate group (C1—O1—$PO_2^-$—O—C), that displays strong anomeric and exo-anomeric effects, diminishes the role of the exo-anomeric effect on the stability of conformers. This finding is in contrast to results on α,α-trehalose, the non-reducing disaccharide resulting from the combination of two α-D-glucopyranose molecules through a (1→1) glycosidic linkage. Conformational analysis of α,α-trehalose revealed [45,46] the synergistic effect of joining two acetal sequences. As a result, the "all-gauche" conformation of the C5—O5—C1—O1—C1'—O5'—C5 segment was found to be the dominant conformer due to additivity of the strong anomeric and exo-anomeric effects. A qualitative rationalization of the conflicting results found for 1 can be obtained considering intramolecular electrostatic interactions. According to this interpretation, the sc conformers about the C1—O1 bond should be destabilized by electrostatic interactions compared to the ap conformer. The ESP charges of the O5 atom and $PO_2^-$ group in 1 depend on the conformation but both are always negative. For example, the ESP charge of the O5 atom is −0.6261 a.u. in the TMGMG conformer and −0.5374 a.u. in the GmGG conformer. Similarly, the effective ESP charge of the $PO_2^-$ group in corresponding conformers is −0.3243 a.u. and −0.3102 a.u., respectively. The O5 . . . P inter-atomic distance is larger in the ap conformation compared to that in the sc conformer (3.74 Å vs. 3.39 Å). Therefore, the repulsive electrostatic interactions between the O5 atom and $PO_2^-$ group are always larger in the latter and destabilize the sc orientation over the ap one. In α,α-trehalose, the effective ESP charge of the corresponding $CH_2$ group is always positive. Consequently, the attractive electrostatic interactions help to stabilize the sc orientation.

The preference of the ap (T) conformer about the anomeric C1—O1 bond for the 2-O-methylphosphono-tetrahydropyran anion represents a unique conformational behavior that has not been previously observed. Such a preference does not occur in other compounds with the C1—X (where X=$CH_2$, O, NH, $NH_2^+$, and S) anomeric linkage.[37] In all these compounds, the sc orientation about the anomeric C1—X bond is preferred over the ap orientation. The preference of the anomeric carbon substituent for the equatorial over the axial orientation has been termed the reverse anomeric effect [47] By analogy, the unusual conformational behavior of the negatively charged phosphate group linked to the anomeric carbon has been termed "the reverse exo-anomeric effect". The magnitude of the exo-anomeric effect can be obtained from a comparison of the sc–ap energy difference in a given compound and in 2-ethyltetrahydropyran (0.9 kcal/mol).[37] Using the 0.9 kcal sc–ap energy difference for the 2-ethyltetrahydropyran, a 2.3 kcal/mol magnitude is estimated for the reverse exo-anomeric effect for the negatively charged phosphate group.

The relation between the anomeric and exo-anomeric effects and the angular dependence of some geometrical parameters has been well established experimentally and theoretically. [21-31] As a consequence of lone pair delocalizations, the rotation about the C1—O1 bond from the sc to the ap conformation increases the C1—O1 bond length and decreases the O5—C1—O1 bond angle in carbohydrates. Similar structural changes are observed in the bond lengths and bond angles for different conformers of 1. These changes are listed in Table 3 and illustrated in FIG. 2. However, they are not so straightforward because there is a subtle interplay between the delocalization of the O1 lone pairs into the anomeric carbon region and/or phosphorus region. Nevertheless, the C1—O1 bond length is the shortest C—O bond. For the same conformation of the phosphate group, for example GG, the C1—O1 bond is shorter in the sc conformation compared to the ap conformation, e.g. in the GGG conformer the C1—O1 bond length is 1.380 Å while it is 1.389 Å in the TGG one. Similarly, the O1—P bond is longer in the ap compared to the sc conformation, e.g. 1.654 Å (TTG) vs. 1.650 Å (TGG). The O1—P bond is also longer than the P—O4 bond. The exceptions are the MGGT, MGMGT, TMGT, and TGT conformers where the conformation about the P—O4 bond is the ap. The key bond angles, O5—C1—O1 and O1—P—O4, are significantly larger in the sc conformers. The O5—C1—O1 angle is approximately 4° larger for the sc (G) conformation (111.8°–114.8°) compared to the ap (T) conformation (108.2°–109.1°). For the O1—P—O4 angle, the smallest angle (94.5°) was found for the GTT conformation where both P—O bonds adopted the ap conformation. The magnitude of the geometrical parameters was also found to be influenced by steric interactions.[35] Values of the C1—O1—P bond angle clearly illustrate their significance. This angle has larger values (133.3°–135.5°) in conformers with the -sc orientation about the C1—O1 bond where the phosphate group lies below the ring. Steric interactions in these conformers are relieved by a 10° increase in the C1—O1—P angle. This illustrates the complexity of the conformational space for 1 and suggests that several factors must be taken together, steric and electrostatic interactions and the anomeric and exo-anomeric effects, in order to explain the conformational properties and geometries of conformers. Inclusion of electron correlation increased the bond lengths by about 0.03 Å but did not change bond angles significantly.

B. Sodium 2-O-methylphosphono-tetrahydropyran (2)

Although there need not be a direct relationship between the lowest energy conformations of 2-O-methylphosphono-tetrahydropyran anion and the structure of sodium 2-O-methylphosphono-tetrahydropyran, the former can be used as a guide for the selection of starting structures for geometry optimization. Thus, in the case of 2, the 27 different staggered conformers were chosen. For the location of the sodium ion, only the position depicted in FIG. 1 has been considered. This choice was based on the previous calculations of dimethyl phosphate and on a survey of phosphate crystal structures. [32,33] In this position, the sodium cation is coordinated directly by two partially charged phosphate oxygens so that electrostatic and charge transfer interactions are maximized.

Among the 27 starting structures, ten of them, namely mGGmG, mGGT, mGmGG, mGTG, mGTmG, mGTT, TGmG, TmGG, TTT, and TGG, collapsed to different optimized conformers which reduced the number of minima to 17. The relative energies and relevant geometrical parameters of these 14 final minima are summarized in Tables 4–6. The calculations of dimethyl phosphate and its sodium salt showed [32,33] that for both systems, the conformations and their relative energies are very similar. The (sc, sc) was the most stable conformer and the (ap, ap) was the least one. The calculations reported here predict a completely different conformational behavior for 2. The most stable structure of 2 appears to be the GTmG completely different from the most stable conformation of 1, TmGmG. In the case of 2, the TmGmG conformer has a relative energy of approximately 4.8 kcal/mol at the 6-31G* level which decreases to 4.1 kcal/mol at the tzp level. Comparison of the results for 1 and 2 in Tables 1–6 revealed other significant differences between both compounds. A completely reversed order of the ap and sc conformers about the C1—O1 bond can be seen from these data. From 17 conformers of 2, the three lowest energy conformers (GTmG, GTG, and GTT) correspond to the sc orientation of phosphorus with respect to the ring oxygen in accordance with the exo-anomeric effect. The conformations adopted by the phosphate group in these three minima are the (ap, -sc) for GTmG, the (ap, sc) for GTG and the (ap, ap) for GTT. The relative energy of the GTG and GTT conformers are 0.4 kcal/mol and 0.9 kcal/mol at both the 6-31G* and tzp/6-31G* levels. The least stable orientation (-sc, MG) about the C1—O1 bond for 2 is the same as for 1. The 6-31G* relative energies of the three conformers having such an orientation about the C1—O1 bond are higher than 11.5 kcal/mol.

The ACM method predicted slightly different relative energies (Table 5), namely 0.5 kcal/mol for GTG and 5.9 kcal/mol for TMGMG at the ACM/6-31 G*//ACM/6-31G* level and very similar values, 0.6 kcal/mol and 5.3 kcal/mol, at the ACM/tzp//ACM/6-31G* level. The corresponding energy differences for the TTG conformer are 6.5 kcal/mol and 6.1 kcal/mol, respectively. The conformational energies for 2, after optimization at the ACM/tzp level, remain very similar to the values obtained with the ACM/6-31G* geometry. Similar to 1, the calculated changes of the zero-point energy and thermal energy between conformations are very small in 2 and do not influence the free energy differences between relevant conformers. Only the entropy term showed significant dependence on the conformation (106.5–121.0 cal/mol.K). After taking into account these vibrational contributions, the free energy differences of the GTG, GTT, and TmGmG conformers relative to the GTmG conformer are 0.1 kcal/mol, 0.3 kcal/mol, and 3.2 kcal/mol, respectively. Thus, for 2, the sc orientation about the C1—O1 is dominant at all levels of computation.

These results indicate that the sugar-phosphate linkage in sodium salt exhibits an exo-anomeric effect about the C—O glycosidic linkage. The qualitative interpretation of the ap preference for 1 based on electrostatic interactions may also be used to rationalize the sc preference for 2. In this context, the complexation of the phosphate group with sodium in 2 compensates the negative charge on the $PO_2^-$ group. Consequently, for the GmGG conformer, the effective ESP charge of the $PO_2^-Na^+$ group is +0.3821 a.u. in 2 compared to −0.5374 a.u. for the $PO_2^-$ group in 1. Therefore, the corresponding electrostatic interactions changed from repulsive in 1 to attractive in 2. As a result, the combination of the exo-anomeric effect and electrostatic interactions has a synergistic effect and leads to a large preference of the sc over the ap conformer. An analysis of the geometry between the sodium and ring atoms revealed that in all conformers having $\Phi$ in sc and $\Psi_1$ in ap orientation the O5 . . . Na distance is ~2.5 Å. Such arrangement observed in the low-energy conformers GTmG, GTG, and GTT allows the sodium atom to interact with the phosphoryl and ring oxygens simultaneously. This indicates that the O5 . . . Na interactions might contribute to the stabilization of these conformers.

The location of the sodium ion varied slightly within the 17 conformers (Table 6). Since the two charged oxygen atoms are not entirely symmetrical, the sodium atom binds in a nonsymmetrical fashion. The O—Na bond lengths range from 2.204 Å to 2.296 Å. The sodium atom is usually slightly displaced from the O2—P—O3 plane in a direction away from the six-member ring and the P—O—Na bond angles are between 85° and 100°. Complexation by sodium induced very interesting deformations in the geometry of the sugar-phosphate linkages. For 2, a comparison of the torsion angles $\Phi$, $\Psi_1$ and $\Psi_2$ with those for the same conformation of 1 shows only slight changes in most cases. An exception is the $\Phi$ angle in some conformers where shifts as large as 40° are observed (for the TGT conformer from 159° in 1 to 121° in 2). Another important feature of the sodium-phosphate interactions emerges from a comparison of the bond lengths of 1 and 2. The most relevant changes are associated with the variation in bond lengths connecting the sugar and phosphate groups (Tables 3 and 6, FIG. 2). Changes for some bond lengths as large as 0.06 Å are predicted between the two compounds. In the sugar part of the sodium complex 2, the C5—O5 and C1—O1 bonds are lengthened, while the O5—C1 bond is shortened compared to the anion 1. For the phosphate part, the O1—P and P—O4 bonds are shortened, while the P—O2 and P—O3 are lengthened in 2. Small variations, less than 5°, are predicted for the O5–C1—P and C1—O1—P bond angles. The O2—P—O3 bond angle narrows from (122°–125°) to (111°–114°) while the O1–P—O4 angle slightly widens from (94°–101°) to (100°–104°). As was found with 1, the inclusion of electron correlation within the ACM method increased the bond lengths approximately by 0.03 Å.

Figure 3:
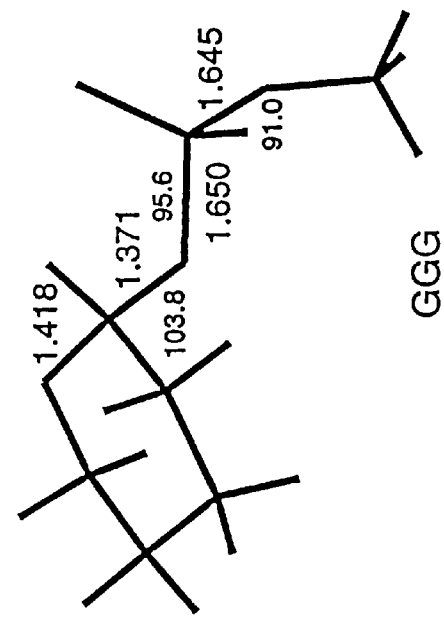
FIG. 3. Comparison of the selected geometry values for the ap and sc lowest energy conformers about the C1—O1 bond calculated using the semi-empirical MNDO method. Bond lengths are given in Angstroms, torsion angles in degrees.
Figure 3:
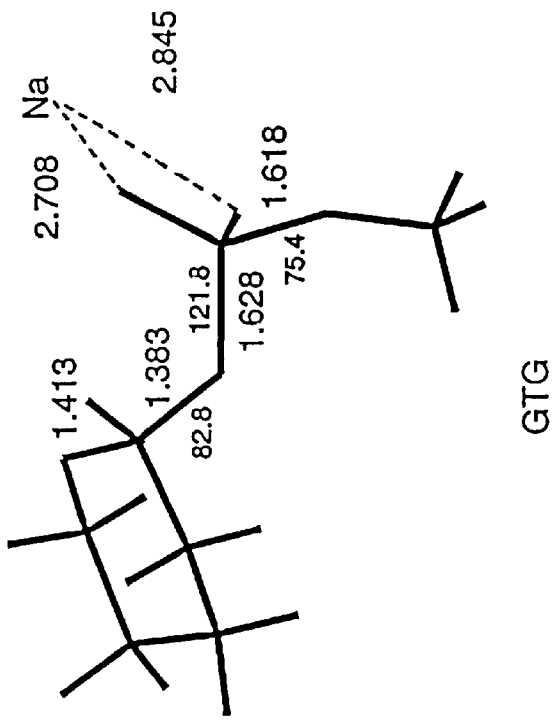
Figure 3:
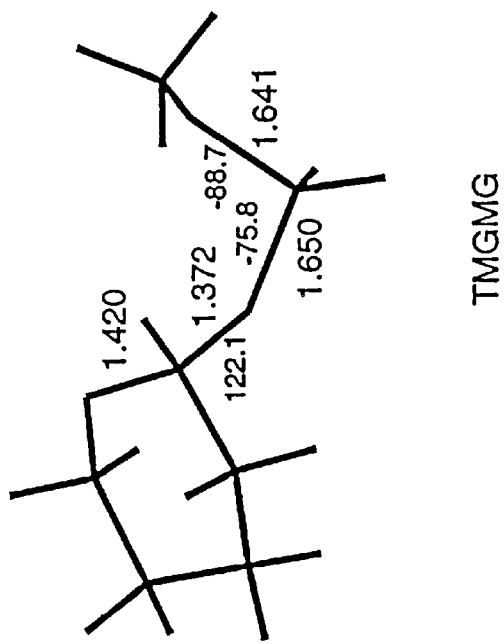
Figure 4:
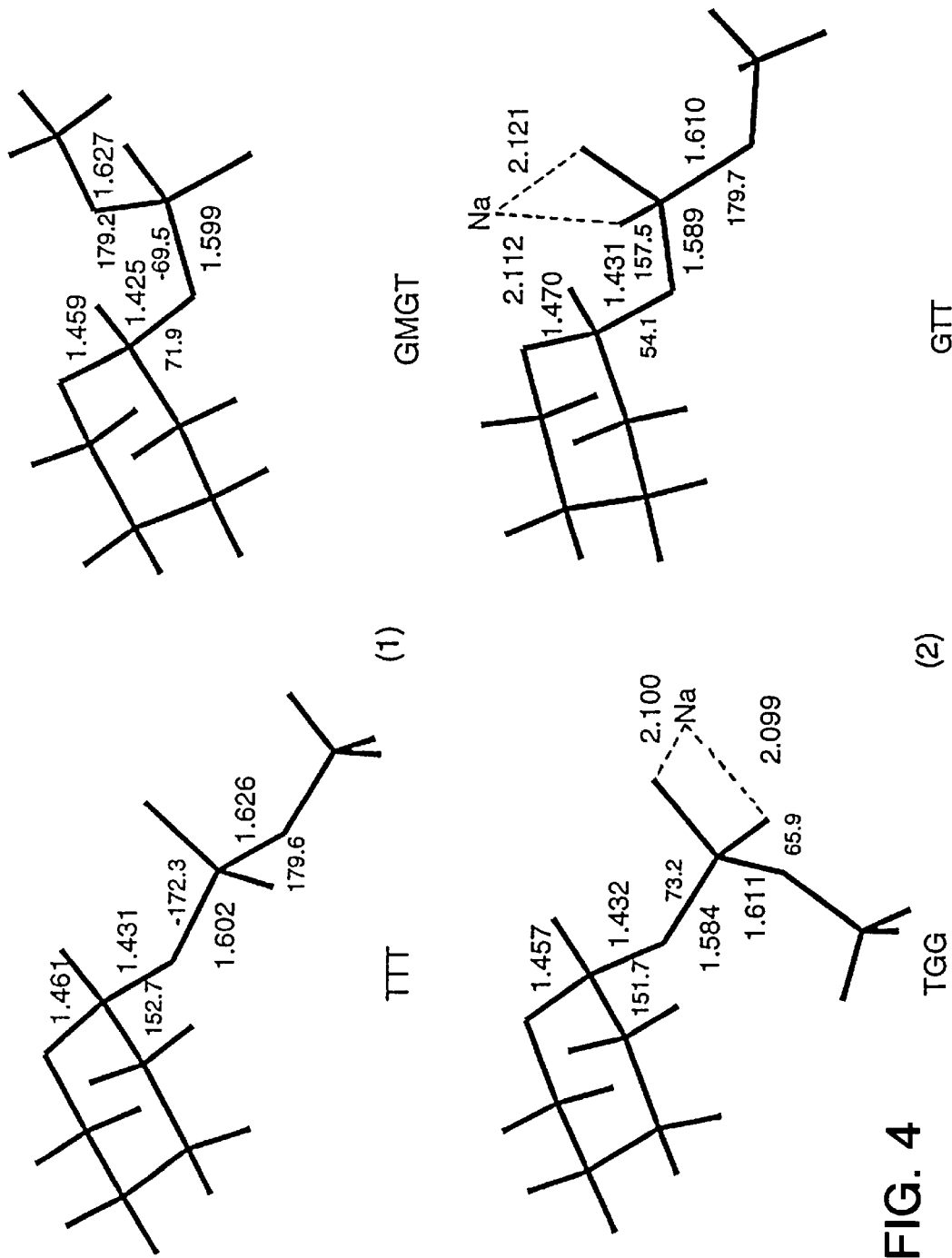
FIG. 4. Comparison of the selected geometry values for the ap and sc lowest energy conformers about the C1—O1 bond calculated using the molecular mechanics method with the CVFF force field ($\epsilon=1$). Bond lengths are given in Angstroms, torsion angles in degrees.
Figure 5:
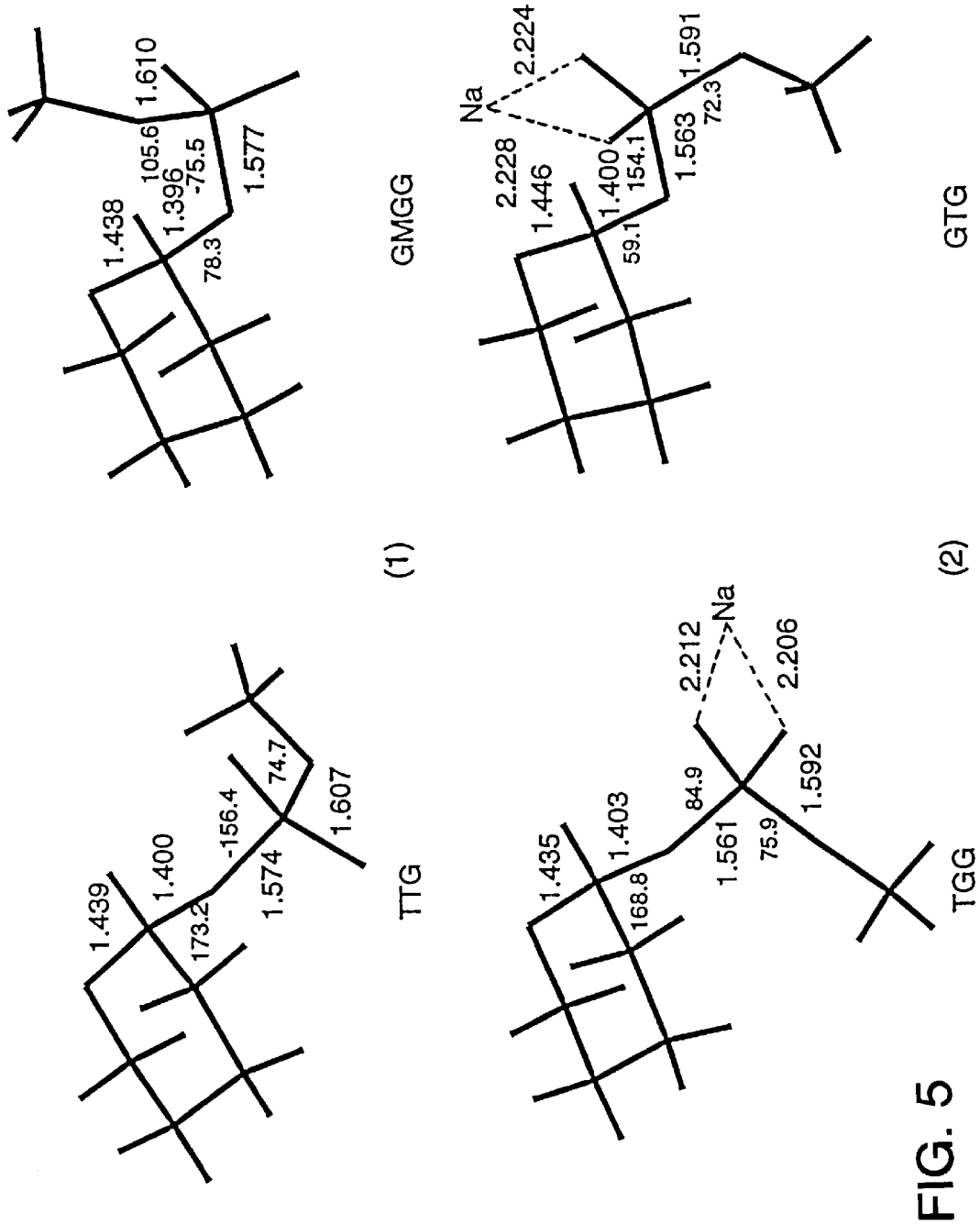
FIG. 5. Comparison of the selected geometry values for the ap and sc lowest energy conformers about the C1—O1 bond calculated using the molecular mechanics method with the AMBER force field ($\epsilon=1$). Bond lengths are given in Angstroms, torsion angles in degrees.

C. Comparison with the Results of Semi-empirical Molecular Orbital and Molecular Mechanics Calculations The large number of heavy atoms and torsion angles in sugar donors such as nucleotide sugars, make high level ab initio calculations of conformational properties for these molecules computationally inaccessible, necessitating the use of less sophisticated computational methods. Additional difficulties are caused by the anomeric and exo-anomeric effects. To model such behavior in complex molecules, it is important to determine the reliability of the predicted relative energies and geometries for the sugar-phosphate linkage as calculated by molecular mechanics programs or semi-empirical molecular orbital methods. In order to answer this question the performance of the MNDO semi-empirical molecular orbital method and molecular mechanics method were examined using the CVFF and AMBER force fields. The calculated relative energies for 1 and 2 are summarized in Tables 7 and 8 and the optimized geometries for the relevant conformers are illustrated in FIGS. 3–5.

The results in Tables 7 and 8 indicate that the preferred orientation about the C1—O1 bond in 1 and 2 calculated using the MNDO method is correctly predicted. The ap orientation is found to be preferred for the 2-O-methylphosphono-tetrahydropyran anion (1) while with the sodium counter-ion present (2), the conformational preference changes completely in favor of the sc orientation. However, in contrast to the ab initio results, conformers with the ap orientation have not been predicted for 2. Another principal difference with ab initio results resides in the reduced number of minima: 10 vs. 16 for 1 and 8 vs. 17 for 2. The lowest energy conformer for 1 (TmGmG) is in agreement with the ab initio results. Nevertheless, the energy differences between the consecutive minima differ. Indeed, the next two low energy minima GGG and GGmG correspond to the sc orientation about the C1—O1 bond with relative energies 0.7 kcal/mol and 1.1 kcal/mol, respectively (Table 7). In the case of 2, the two lowest energy minima, GTG and GTmG, display the sc orientation with respect to the C1—O1 bond but, contrary to the ab initio results, GTG is the preferred. The GTmG conformer is 0.8 kcal/mol higher in energy than the GTG conformer using the MNDO method but it is lower by 0.4 kcal/mol at the 6-31G* level. The geometrical features observed for 1 and 2 show the same overall geometrical trends compared to those observed by ab initio calculations. The C1—O1 bond is lengthened in 2 compared to that in 1, whereas the O1—P bond is shortened (FIG. 3) and the O2—P—O3 angle narrowed. A comparison of the torsion angles reveals differences in the exact location of the minima in $\Phi$ dihedral space as predicted by the MNDO and the ab initio methods. For example, in the sc orientation, the MNDO values of the Φ torsion angle are close to 100°, whereas the corresponding 6-31G* values are closer to 60°. Similarly, slight differences between the magnitude of bond lengths and bond angles predicted by semi-empirical and ab initio calculations are observed. The C1—O1 bonds are usually predicted approximately 0.01 Å shorter and the O1—P bonds 0.02 Å longer than the corresponding 6-31G* values. For the bond angles, the most remarkable difference was found for the C1—O1—P angle that is approximately 10° larger in MNDO structures. On the other hand, MNDO values adequately describe the structural trends observed between 1 and 2 in the ab initio calculations.

The relative energies of the conformers of 1 and 2 obtained by molecular mechanics calculations using CVFF and AMBER force fields are summarized in Tables 7 and 8. The geometry of the lowest energy conformer for the ap and sc orientation around the C1—O1 bond is illustrated in FIGS. 4 and 5. Larger number of minima were found for both compounds 1 and 2 by these methods compared to the ab initio results. Both molecular mechanics methods provided different results and incorrectly predicted the lowest energy conformer for 1. As well, the relative energies of the conformers for the 2-O-methylphosphono-tetrahydropyran anion calculated by CVFF and AMBER methods are in poor agreement with ab initio results. Nevertheless, both force fields (except the CVFF force field with $\epsilon=4$) correctly predicted the ap orientation about the C1—O1 bond as the most favored for 1. In contrast, both methods failed to describe accurately the energies of conformations about the phosphate linkages. For 2, both force fields seem to give reasonable results. However, in most of the cases, the three lowest conformations from ab initio results (GTMG, GTG and GTT) are predicted in a different order by molecular mechanics. It can be seen from Tables 7 and 8 that the change of dielectric constant from 1 to 4 significantly altered the relative energies of conformers calculated by both force fields. In general, for $\epsilon=4$, the energy differences are predicted to be significantly smaller (up to 5 kcal/mol) and in disagreement with the ab initio results. Since an increase of $\epsilon$ decreases intramolecular electrostatic interactions, this suggests an important role for these interactions in stability of conformers in 1 and 2. It is also interesting to note that the stabilization of the sc orientation about the C1—O1 bond relative to the ap increased with the dielectric constant for both 1 and 2. The purpose of this comparison has been to estimate the reliability of semi-empirical molecular orbital and molecular mechanics methods to model the sugar-phosphate linkage. The results suggest that none of the molecular mechanics methods used reproduce in a satisfactory way the ab initio results. From the comparison of the results summarized in Table 7 and 8, it seems that the semi-empirical MNDO method gives the closest results to ab initio ones, at least in a qualitative way.

D. Implications Concerning the Catalytic Mechanism of Glycosyltransferases

Kinetic studies with some transferases [6,8,11-13] indicate a largely ordered sequential mechanism, with the sugar donor binding first. For most transferases the presence of a metal cofactor has been shown to be required and furthermore the metal binds to the enzyme prior to the donor nucleotide-sugar. Then, before any of the products leave the enzyme, a sugar acceptor has to be bound. The metal cofactor is released from the enzyme in the form of a complex with the nucleotide-phosphate. It would appear that these experimental findings and the predicted changes in conformational behavior between 1 and 2 are not coincidental. It is suggested that the complexation of a positive metal cation with the negatively charged phosphate group in the sugar donor molecule represents an important step in the mechanism of glycosyltransferases. The complexation of phosphate with the metal ion would appear to fulfill three different purposes. One purpose could be to change the conformation in order to adopt the correct shape for optimal enzymatic recognition and thereby achieve maximal catalytic efficiency. A second possibility is to activate the C1—O1 bond for cleavage by the enzyme. The third possible purpose is to enable the protonation at the glycosidic phosphate oxygen to begin the scission of the C1—O1 glycosidic bond. In 1, the protonation of O1 would be relatively unfavorable because of the competition from the partially charged phosphate oxygens.

It is generally assumed that one of the important aspects of enzymatic catalysis is the binding of the substrate and its conversion into a reactive conformation. Assuming that the sc conformation about the C1—O1 bond is more reactive than the ap one, then the enzyme has to distort 1 into a less populated and higher energy conformation. During this binding several rotational degrees of freedom must also be lost. Both, the enthalpic and entropic internal effects are unfavorable for the reaction rate. However, as shown in previous sections, complexation with sodium reverses the conformational equilibrium. In the case of 2, the sc orientation is dominant and relative energy of the ap orientation (4 kcal/mol) is significantly higher. Since the structure of 2 is restricted into the most reactive conformation, unfavorable entropic effects from this rotational degree of freedom (the rotation about the C1—O1 bond) should be lower in 2 compared to 1. This might give an estimated 2–4 kcal/mol in favor of cleavage via the sc conformation relative to the ap one. In this qualitative argument the enthalpic considerations from the phosphate group have been ignored. However, as shown above, the energy differences between the conformers of the phosphate group are quite modest compared to those about the C1—O1 bond.

Figure 2:
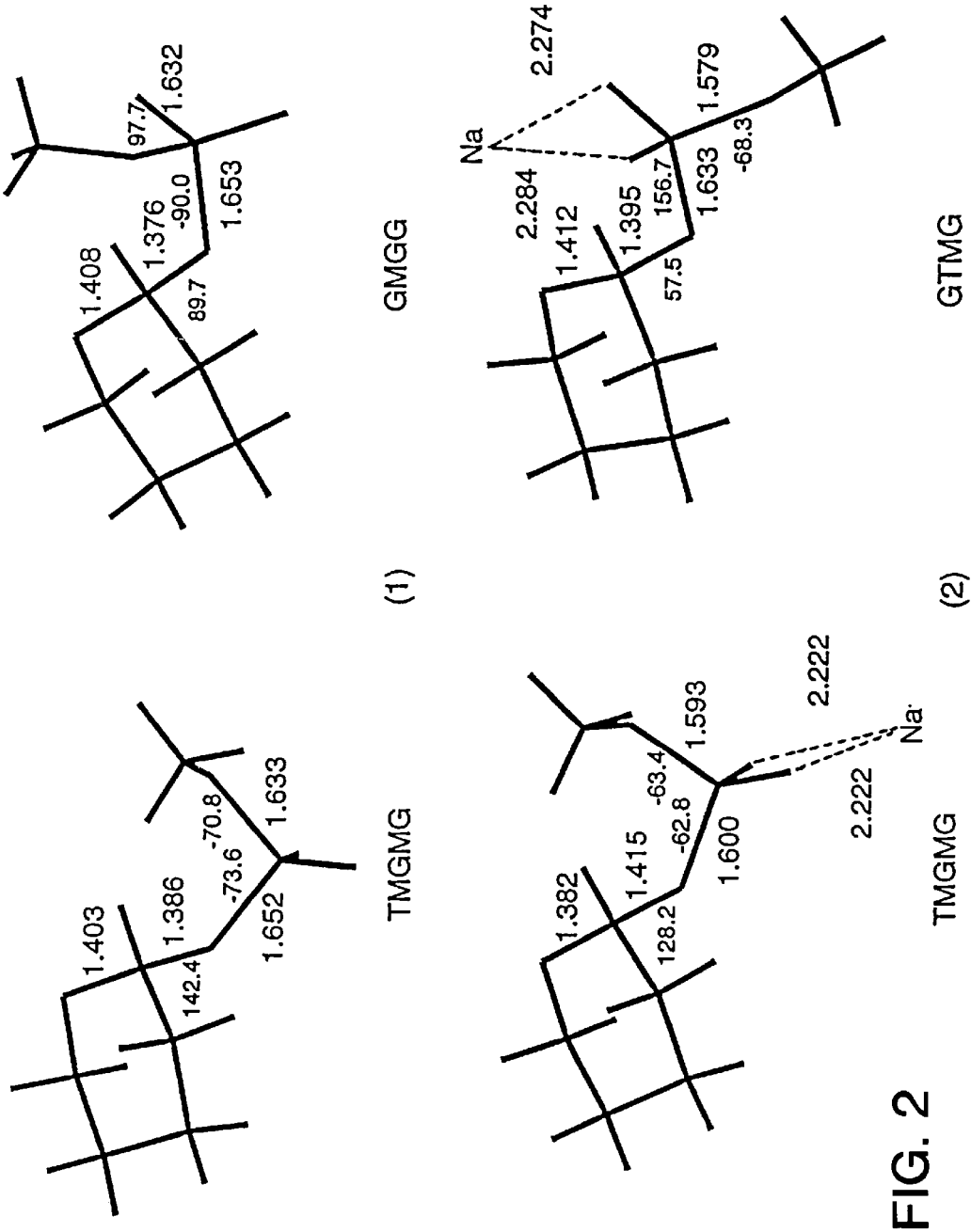
FIG. 2. Comparison of the selected geometry values for the ap and sc lowest energy conformers about the C1—O1 bond calculated using the ab initio method at 6-31G* level. Bond lengths are given in Angstroms, torsion angles in degrees.

Ab initio modeling of the sugar-phosphate linkage using 1 and 2 at the 6-31G* revealed that the C1—O1 bond length between the anomeric carbon and glycosidic oxygen elongates by 0.02 Å and that the O1—P bond between the glycosidic oxygen and phosphorus shortens by 0.02 Å upon formation of the complex. In this context, the complexation with sodium imposes a perturbation of the geometry for the sugar phosphate linkage along the reaction coordinate of the catalytic reaction towards the transition state. This is illustrated in FIG. 2 where the structures and selected geometrical parameters for lowest energy conformers of 1 and 2 are presented. The C1—O1 bond is cleaved during the catalytic reaction. Therefore, its elongation activates this bond and decreases the reaction barrier. A similar effect might be expected from the shortening of the O1—P bond length since this bond is shorter in the product of this reaction, sodium methyl phosphate (1.6073 Å), compared to its magnitude in 1 or 2. For spontaneous acetal hydrolysis, the relationship between the C1—O1 bond length and the free energy of activation has been established. [48,49] It has been argued that small changes in the C1—O1 bond lengths decrease the reaction barrier as much as 10 kcal/mol per 0.05 Å. This gives an upper estimate of 3–5 kcal/mol in the decrease in the reaction barrier by complexation with sodium.

The above suggests that the theoretically predicted differences in geometry and conformational equilibrium between 1 and 2 might be a prerequisite for the binding of the sugar donor to the enzyme and to begin the catalytic reaction. The difference between the reactivity of different substrates (e.g. case, 1 and 2) is given by the differences between the ground and transition state free energies.

Conclusions

The geometry and energy of conformers around the three bonds, C1—O1, O1—P, and P—O4, joining the sugar and phosphate group in the 2-O-methylphosphono-tetrahydropyran anion (1) and sodium 2-O-methylphosphono-tetrahydropyran (2) have been obtained at various SCF and ACM DFT levels of ab initio calculations. The free energy of the conformers has been calculated by evaluating the zero-point energy, thermal energy, and entropy contributions at 6-31G*.

For the 2-O-methylphosphono-tetrahydropyran anion (1), the preference of the ap over the sc orientation about the C1—O1 bond has been predicted at all levels of ab initio calculations. This unusual phenomenon has been termed, by analogy with the reverse anomeric effect, as the reverse exo-anomeric effect. The 2.3 kcal/mol magnitude of this effect has been estimated for the negatively charged phosphate group. For the sodium 2-O-methylphosphono-tetrahydropyran (2), all calculations have predicted the dominance of the sc over the ap orientation about the C1—O1 bond in accordance with the exo-anomeric effect. Structural variations in geometrical parameters have shown changes characteristic for the anomeric and exo-anomeric effects.

Differences in the structure of the 2-O-methylphosphono-tetrahydropyran anion (1) and sodium 2-O-methylphosphono-tetrahydropyran (2) suggest an important function for the metal cofactor in the catalytic mechanism of transferases. Three different roles of the cofactor have been postulated: causing a change in the conformation for optimal bonding to the enzyme, activating the C1—O1 glycosidic bond by elongating the C1—O1 bond, and changing the charge distribution to make the protonation of the O1 glycosidic oxygen more favored.

EXAMPLE 2

Figure 6A:
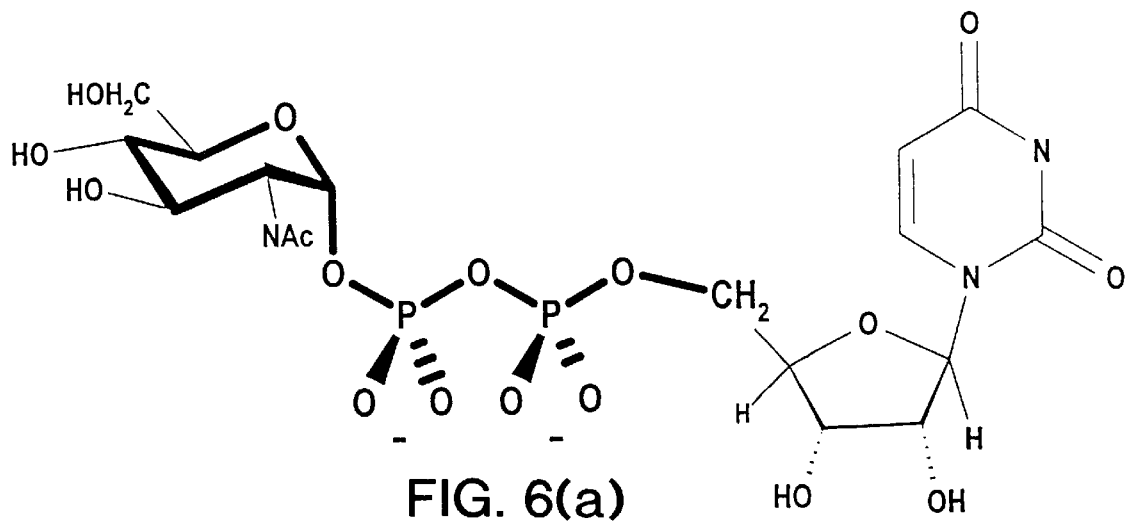
FIG. 6 is a schematic representation of (a) uridine diphosphate-N-acetylglucosamine (the highlighted part has been modeled in this work), (b) 2-O-methyldiphosphono-tetrahydropyran dianion (3) and (c) magnesium 2-O-methyldiphosphono-tetrahydropyran (4).

Effects of the Complexation by the $Mg^{2+}$ Cation on the Stereochemistry of the Sugar-Diphosphate Linkage. Ab Initio Modeling on Nucleotide-Sugars Models and Computational Procedures The conformational behaviour of the diphosphate functional group linked to the anomeric carbon in hexopyranosides has been studied with ab initio methods using the 2-O-methyldiphosphono-tetrahydropyran dianion (3) and the magnesium 2-O-methyldiphosphono-tetrahydropyran (4) as models. Structures of the compounds with axially oriented diphosphate groups are illustrated in FIG. 6 together with the UDP-GlcNAc [uridine 5'-(2-acetamido-2-deoxy-α-D-glucopyranosyl pyrophosphate)] representing nucleotide diphosphate sugars. For a description of the atoms (FIG. 6) the atom numbering used in the carbohydrate nomenclature are used, where the anomeric carbon is denoted as C1, etc. By the analogy with the glycosidic linkage of oligosaccharides, the term "sugar-phosphate linkage" is used for the C1—O1—P3 bonds. Two dihedral angles outline the conformations around this linkage. The rotation about the anomeric C1—O1 linkage is described by the dihedral angle $\Phi[\Phi=\Phi(O5—C1—O1—P3)]$ and the orientation about the O1—P3 bond by the dihedral angle $\Psi_1[\Psi_1=\Psi_1(C1—O1—P3—O4]$. Orientations of the diphosphate group are described by two dihedral angles $\Psi_2[\Psi_2=\Psi_2(O1—P3—O4—P5)]$ and $\Psi_3[\Psi_3=\Psi_3(P3—O4—P5—O6)]$. Finally, the dihedral angle $\Psi_4[\Psi_4=\Psi_4(O4—P5—O6—C)]$ describes the orientation of the terminal methyl group which in this case models the methylene group of the nucleoside part of sugar-nucleotides. Conformations of compounds 3 and 4 are then described using five torsion angles $\Phi, \Psi_1, \Psi_2, \Psi_3$, and $\Psi_4$. Three staggered orientations about the C1—O1 and P—O bonds are denoted as G (synclinal, gauche, 60°), T (antiperiplanar, trans, 180°), and mG (-synclinal, -gauche, -60°), respectively. The eclipsed orientations about these bonds are denoted as C (synperiplanar, cis, ~0°), A (anticlinal, ~120°), and mA (-anticlinal, ~-120°), respectively. In this notation, e.g., AGTmGmA means that the angles $\Phi, \Psi_1, \Psi_2, \Psi_3$ and $\Psi_4$ are approximately in the anticlinal (ac, A), synclinal (sc) or gauche (G), antiperiplanar (ap) or trans (T), -synclinal (-sc) or -gauche (mG), and -anticlinal (-ac, mA) conformation, respectively.

The ab initio calculations were carried out with the Turbomole 95.0 and GAMESS programs using standard basis sets. The optimisation of the geometry was performed at the SCF level with the 6-31G* basis set. The geometry was fully optimised using the gradient optimisation routines of the program without any symmetry constraints. For several relevant minima of 3 and 4, more extensive calculations using different methods and different basis sets were performed using the Jaguar program (Jaguar, 3.5 S., Inc. Portland, Oreg., 1998). The vibrational frequencies were calculated at the HF/6-31G* level and the zero-point energy, thermal and entropy corrections were evaluated. The relevant conformers were also calculated using a hybrid Hartree-Fock-density functional scheme, the adiabatic connection method B3LYP [41] of density functional theory [42] (DFT). The standard 6-31G and 6-31++G basis sets were utilized for the geometry optimization. Single point calculations were carried out with the cc-pVTZ(-f)++ basis set for 3. Local MP2 calculations [60] were then performed on these geometries with the cc-pVTZ(-f)++ basis set for 3 and with the 6-31++G basis set for 4. Thus, electron correlation effects were treated by means of DFT and LMP2. The solvent effects on the conformational equilibrium have been investigated with a self-consistent reaction field method [61] as implemented in Jaguar at B3LYP/6-31G level. Solvation calculations were carried out for two solvents, namely cyclohexane ($\epsilon$=2.023) and water ($\epsilon$=80.37) using the geometries calculated in gas phase.

Results and Discussion

A. 2-O-methyldiphosphono-tetrahydropyran Dianion (3)

Figure 6B:
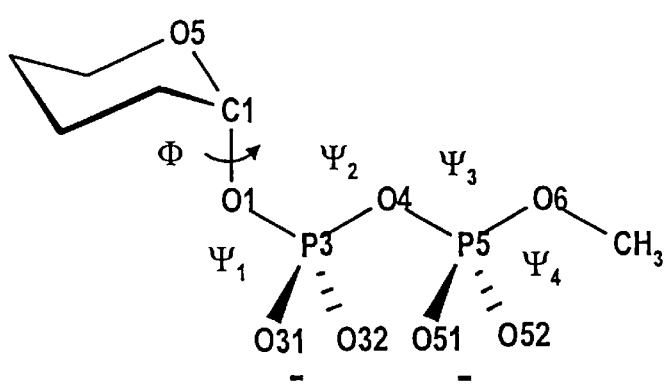
Figure 6C:
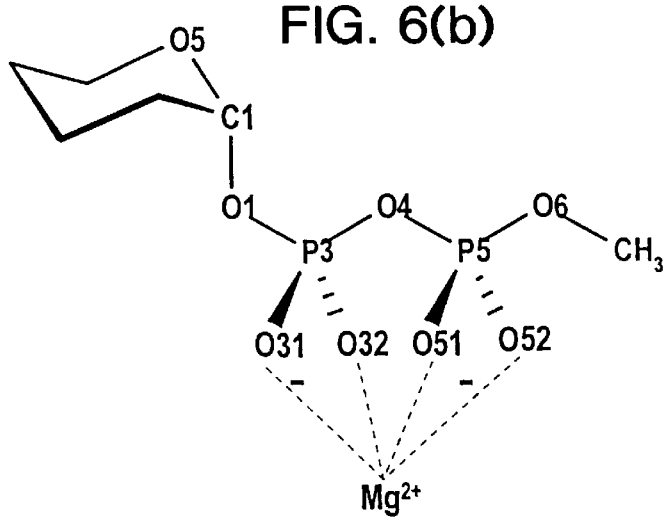

The conformation of the sugar-diphosphate and diphosphate linkages in the 2-O-methyldiphosphono-tetrahydropyran dianion (1) is described by five internal rotational degrees of freedom, associated with the C1—O1, O1—P3, P3—O4, O4—P5 and P5—O6 bonds (FIG. 6b). The assumption of three staggered conformers for each bond would generate 243 ($3^5$) conformers to be considered. A systematic grid search using high level ab initio calculations of these conformers would require excessive computer time. Therefore, the previous results were utilized on structurally related models, the 2-O-methylphosphono-tetrahydropyran anion and the dimethyl diphosphate dianion as a guide to restrict the conformational space of 3. The study of the first molecule gave important information on the preferred orientations observed about the sugar-phosphate linkage ($\Phi$, $\Psi_1$ dihedral angles), whereas the study of both molecules provided data on the more favourable conformation of the diphosphate linkages ($\Psi_2$ and $\Psi_3$ dihedral angles). The combination of all this information reduced significantly the number of conformers by providing simply 100 starting structures for geometry optimisations. Three staggered conformations around the C1—O1 bond have been calculated for the 2-O-methylphosphono-tetrahydropyran anion, namely the sc, ap, and -sc orientations. Conformers adopting the -sc orientation about the C1—O1 bond have higher relative energy (6.7–9.4 kcal/mol) due to the presence of unfavourable steric interaction of the phosphate group with pyranoid ring atoms. It was presumed that such interactions might be more severe for the larger diphosphate group. Indeed, preliminary calculations of several conformers with the -sc orientation showed that the optimisation changed the orientation around the C1—O1 bond from the -sc to the ap conformation. Therefore, during the generation of the starting conformations of 3, the -sc orientation for the $\Phi$ dihedral angle has not been considered. The calculated relative energies and dihedral angles of the final 6-31G* minima are gathered in Table 9.

Figure 7:
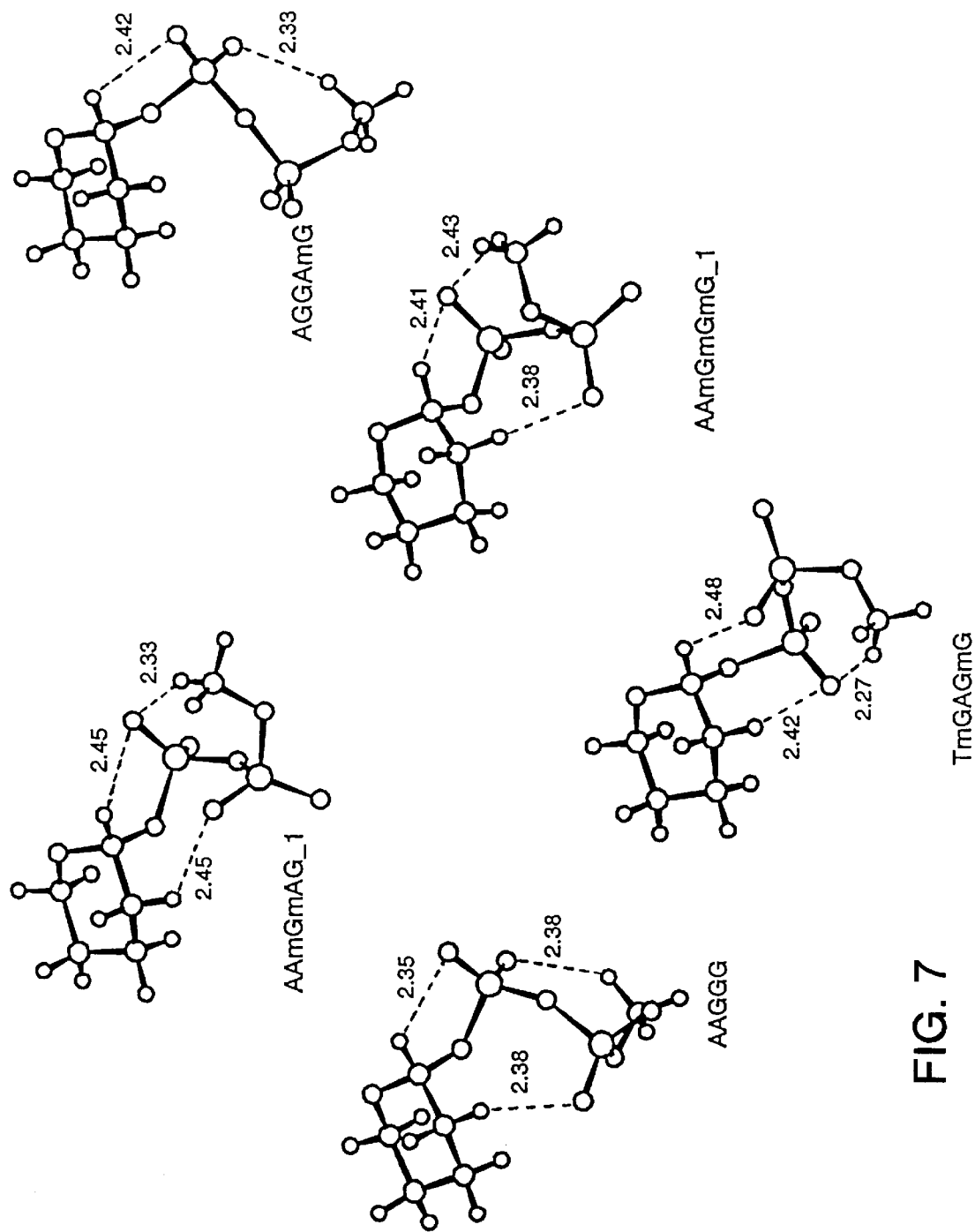
FIG. 7 is a representation of the hydrogen bonding patterns observed for the five lowest energy conformers of the 2-O-methyldiphosphono-tetrahydropyran dianion (3) calculated using the ab initio method at 6-31G*. Dashed lines show the CH . . . O hydrogen bonding interactions. Bond lengths are given in angstroms.

As shown in Table 9, the optimisation of the 100 starting structures at the HF/6-31G* level led to 37 distinct minima. Energies of all minima cover a relatively small interval of 8.5 kcal/mol. This suggests that the sugar-diphosphate linkage in 1 is quite flexible but this flexibility is restricted to a small part of the potential energy hypersurface. Analysis of the results also indicates that transitions between different conformers about the O1—P4—O5—P5—O6 bond sequence require a concerted rotation about at least two bonds with exception of the $\Psi_4$ dihedral angle describing the free rotation of the external methyl group. Results of the present study show an unusual conformational behaviour of the sugar-diphosphate linkage that has already been observed for the 2-O-methylphosphono-tetrahydropyran anion. The diphosphate group linked to the anomeric carbon prefers the anticlinal (~120°, ac) over the synclinal orientation about the anomeric C1—O1 bond. Such a preference for the ac conformer about the C1—O1 bond observed in sugar-phosphate linkages is unique among the conformational behaviour of glycosyl compounds [37] and this phenomenon has been named as the reverse exo-anomeric effect. The anticlinal conformers around the C1—O1 bond can be divided into two groups. The first and more frequent group corresponds to the so-called trans conformation ($\Phi$~150°) observed in a-glycosyl compounds. The second and less frequent group ($\Phi$~100°) represents a unique conformation found around the anomeric bond. The four lowest energy conformations (AAmGmAG, AGGAmG, AAGGG, and AAmOmGmG) show the same orientation around the C1—O1 bond with $\Phi$~104–154° (ac) and around the O1—P3 bond with $\Psi_1$~83–108° (sc, ac) (FIG. 7). These four lowest energy conformers exhibit a clear deviation from the ideal gauche position (sc, 60°) and their relative energies are within only 1.3 kcal/mol. From Table 9, it is clear that the sc orientation around the C1—O1 bond is not favoured. Indeed, it appears that from 37 final minima, only seven minima adopted the gauche conformation about the C1—O1 bond. The lowest energy conformer (GmAmGmGG) with the sc orientation is 2.8 kcal/mol above the AAmGmAG conformer, which is the lowest energy conformer for the ac orientation.

Previous high level ab initio calculations performed on monophosphated derivatives have shown a clear preference of the P—O bonds in the C—O—P—O—C bond sequence for the sc conformation. For diphosphate linkages, results have shown a similar dominance of the sc orientation for the P—O bonds in the O—P—O—P—O bond sequence. As it can be seen in Table 9, only a few conformers adopted the ap orientation around the P—O bond. This conformation appears to be considerably less stable than the sc orientation.

In a general way, phosphated derivatives in their anionic forms exhibit a strong preference for the sc over the ap conformation around the P—O bond in accordance with the general anomeric effect. However, in contrast with the results on the dimethyl diphosphate dianion, one of the P—O bonds in 1 is usually shifted from the sc to the ac conformation. The (sc, ac) or (-sc, -ac) arrangements of the O1—P3—O4—P5—O6 segment are present in the two lowest energy conformers (AAmGmAG and AGGAmG) with ($\Psi_2$, $\Psi_3$)=(-60°, -102°) and (64°, 93°), respectively. The next two conformations (AAGGG and AAmGmGmG) present another conformation around the P—O—P segment, namely, the sc, sc and -sc, -sc. The corresponding values of dihedral angles are (47°, 18°) and (-45°, -39°), respectively. All these arrangements correspond to conformations observed for the dimethyl diphosphate dianion. Based on the relative energy of these conformers, it was assumed that the potential energy surface about the $\Psi_2$, $\Psi_3$ dihedral angles to be a very flat region. Thus, interactions with environment (protein, counterion, or solvent) can change conformational preference around these linkages.

Inspection of the three-dimensional structure of the lowest energy conformations of 3 reveals the presence of stabilising interactions between phosphate oxygen atoms and one of the hydrogens attached to a carbon atom, i.e. C—H . . . O hydrogen-bonding interactions. Among the low energy conformers, distinct hydrogen bonding patterns are observed. Apparently, these patterns are closely related to the conformation observed around the sugar-phosphate linkage ($\Phi$ and $\Psi_1$ dihedral angles). For instance, the four lowest energy conformers (AAmGmAG, AGGAmG, AAGGG, and AAmGmGmG) with the (ac, ac) orientation around the sugar-phosphate linkage, display a same hydrogen-bonding pattern. As it can be seen on FIG. 7 where selected conformers are shown, three CH . . . O interactions are usually present in this group of conformers involving charged phosphoryl oxygen atoms of both phosphate groups with several hydrogens. The relevant geometrical parameters for the different interactions displayed on FIG. 7 are C1—H1 . . . O—P3($d_{H...O}$~2.4 Å, $\theta_{C-H...O}$~100–110°), CH3 . . . O—P3($d_{H...O}$~2.3–2.4 Å, $\theta_{C-H...O}$~130–155°) and C2—H2 . . . O—P5($d_{H...O}$~2.3–Å, $\theta_{C-H...O}$~130–150°). The lowest energy conformer with the ap conformation around the C1—O1 linkage, TmGAGmG, displays a distinct hydrogen bonding motif (FIG. 2). Three CH . . . O interactions are again surveyed though they involve different atoms. The geometrical parameters characterising the interactions shown on FIG. 7 are C1—H1 . . . O—P5($d_{H...O}$~2.5 Å, $\theta_{C-H...O}$~125°), CH3 . . . O—P3($d_{H...O}$~2.3–2.4 Å, $\theta_{C-H...O}$~147°) and C2—H2 . . . O—P3($d_{H...O}$~2.3–2.4 Å, $\theta_{C-H...O}$~120°). Geometrical parameters observed are characteristic of the CH . . . O hydrogen-bonding interactions described in the literature [55,62]. The comparison of both patterns observed reveals very similar short (C—)H . . . O contacts but involving different phosphoryl oxygen atoms in each case. These patterns can almost be considered as inverted. Clearly, conformations of diphosphate groups are stabilised by such interactions.

In order to claify the importance of these interactions in the stabilisation of anionic phosphate derivatives, these patterns were compared with similar structural features observed in the dimethyl diphosphate dianion. The dimethyl diphosphate dianion is a symmetric molecule ended with methyl groups on both extremities and conformations of the molecule are not influenced by the presence of a sugar unit. The main factor controlling the overall conformation of such molecule is the flexibility around the P—O—P segment. For this molecule, the preferred arrangement for the O—P—O—P—O bond segment ($\Psi_2$ and $\Psi_3$ dihedral angles) is (sc, sc) or its symmetrically related conformation (-sc, -sc). In spite of a slight shift from the ideal 'staggered' position, the dimethyl diphosphate dianion exhibits a similar preference for the synclinal conformation around the phosphate linkage as well as almost identical intramolecular hydrogen bond patterns. Both phosphate groups are stabilised by CH . . . O(—P) interactions involving the two external methyl groups. For instance, the lowest energy conformers of the dimethyl diphosphate dianion (mGGGmG and GGGG) show the presence of two symmetrical short contacts ($d_{H\ldots O}$=2.3 and 2.4 Å resp.) involving each of the phosphate groups with the farthest methyl group. Obviously the occurrence of C—H . . . O(—P) interactions in these structures is not fortuitous and it definitely points out the role they might have in the stabilisation of phosphate derivatives. Such long-range hydrogen bonding interactions have often shown their great importance in crystal engineering [55, 63].

Recent calculations on carbohydrate model compounds [37] and dimethyl diphosphate [32] suggested that calculations with the 6-31G* basis sets at HF level provide a reasonable set of conformational energies and geometries. Calculations on the sugar-monophosphate linkage and the diphosphate linkage also support this suggestion. On the other hand, because a dianion is involved in the system investigated, the inclusion of diffuse functions should give more reliable results [54]. Therefore, to test the reliability of the results calculated at the HF/6-31-G* (272 basis functions) level, a series of calculations was run on five representative conformers, namely AAmGmAG, AGGAmG, AAGGG, AAmGmGmG, and TmGAGmG, at the HF/6-31++G (384 basis functions), HF/cc-pVTZ(-f)++ (676 basis functions), and LMP2/cc-pVTZ(-f)++ levels. Density functional theory based on adiabatic connection arguments, which incorporates an admixture of Hartree-Fock exchange in a linear combination with the usual density functional ingredients [41], have been shown to provide good quality geometries. Therefore, the B3LYP/6-31G (308 basis functions) and the B3LYP/6-31++G** levels were also utilised for geometry optimisation and the B3LYP/cc-pVTZ(-f)++ level for single point calculations of the energy. Results of these calculations are shown in Tables 10 and 11.

The selected geometrical parameters for five conformers of 3 indicate that the change in geometry when going from the HF/6-31G* level to the HF/6-31++G, B3LYP/6-31G or B3LYP/6-31++G** levels is rather small. Usually the change in any torsional angle is less than 15°. An exception is however the $\Psi_3$ torsional angle of the AAmGm-mGmG and AGGAmG conformers where larger differences were observed. Differences in the bond angles calculated at all levels of theory are within 5°. Comparison of bond lengths revealed that the trends observed in the geometries at the HF/6-31G* level remain at the HF/6-31++G, B3LYP/6-31G and B3LYP/6-31++G** levels. It is noteworthy, however, that the HF/6-31G* bonds are systematically shorter than the B3LYP/6-31G** bonds. For example, the C—O bond is typically shorter by 0.02 Å (1.376 Å–1.398 Å versus 1.398 Å–1.419 Å) and the P—O single bond lengths are typically 0.03 Å to 0.04 Å shorter (1.612 Å–1.652 Å versus 1.648 Å–1.703 Å). Such a systematic difference was also noticed in previous calculations and is likely characteristic of the 6-31G* basis set. Further expansion of the basis set by adding diffuse functions does not alter bond lengths. Indeed, the bond lengths observed at HF/6-31G* versus HF/6-31++G level and at B3LYP/6-31G versus B3LYP/6-31++G** level are roughly the same.

Table 10 presents the relative energies for the seven conformers of 3 calculated at different levels. Comparison of the relative energies shows that an increase of the basis set decreases energy differences. The HF/6-31G* energies display the largest differences observed (up to 0.85 kcal/mol) with the LMP2/cc-pVTZ(-f)++//6-31++G** results. Inclusion of the diffuse functions into the basis set, i.e. 6-31G* versus 6-31++G**, significantly decreases these differences. This is also observed for single point calculations when using the HFl6-31G* geometry. These findings together with the large deviations observed in the $\Psi_3$ dihedral angle of some conformers suggest that the basis sets with diffusion functions are more appropriate than the 6-31G*. basis set for accurate prediction of the structure and relative energy of dianionic diphosphate systems. Despite the general agreement, both HF and DFT methods erroneously predict the lowest energy conformer compared to the LMP2 method. The LMP2/cc-pVTZ(-f)++//6-31++G** results show a preference for the AGGAmG conformer over the AAmGmAG by 0.14 kcal/mol. At all levels of HF and DFT/B3LYP calculations, the AAmGmAG is predicted as the lowest energy conformer. This preference increases from 0.3 kcal/mol to 0.7 kcal/mol.

The influence of the solvent on the relative stability of conformers around the C1—O1 bond in carbohydrate derivatives is well documented [64]. In order to provide insight on the importance of the solvent effects on the stability of the sugar-phosphate linkage conformers, the solvation energies for seven selected conformers of 3 were calculated using the B3LYP/6-31G** method and the Jaguar program. These results together with the calculated zero-point vibrational energies, the thermal energies and the entropies at 6-31G* level are given in Table 11. Examination of the data in Tables 10 and 11 clearly revealed that after considering the thermodynamic corrections, the AGGAmG is the preferred conformer. At the three highest levels of theory here calculated the HF/cc-pVTZ(-f)++//6-31++G, B3LYP/cc-pVTZ(-f)++//6-31++G and LMP2/cc-pVTZ(-f)++//6-31++G**, the gas phase relative energies are 0.32 kcal/mol, 0.51 kcal/mol, and -0.14 kcal/mol respectively. After including the zero-point vibrational energies, thermal energies and entropies, calculations predict the relative free energy of the AGGAmG conformer to be -0.24 kcal/mol, -0.05 kcal/mol, and -0.69 kcal/mol, respectively. As it can be seen in Table 11 there is a 2 kcal/mol variation in the predicted solvation energies of the conformers in cyclohexane solution and a 5.5 kcal/mol variation in aqueous solution. Calculated solvation free energies in water (from -200.8 kcal/mol to -205.4 kcal/mol) are in accordance with the value of -195.8 kcal/mol calculated by the polarised continuum model for the pyrophosphate dianion [65]. The preference for the AGGAmG conformer is clearly more pronounced in solution than in gas phase. Both of the solvents here mentioned stabilise this conformer since at the highest level of theory, this conformer is preferred by 0.65 kcal/mol in cyclohexane and by 1.94 kcal/mol in water.

Magnesium 2-O-methyldiphosphono-tetrahydropyran Complex (4)

The inclusion of a magnesium cation into the molecule 3 introduces new conformational variables such as the possibility of several locations for the $Mg^{2+}$ with respect to the diphosphate group. This considerably complicates the conformational analysis of the magnesium 2-O-methyldiphosphono-tetrahydropyran complex (4) (FIG. 6c) compared to 3. In order to restrict the complexity of the conformational space into a more manageable dimension, previous results on a related model, the magnesium dimethyl diphosphate complex were used. The most favourable conformations of the diphosphate linkage ($\Psi_2$ and $\Psi_3$ dihedral angles) and the locations occupied by the magnesium cation in this molecule have been used as templates to generate the starting structures for geometry optimisation of 4. Such as in the case of 3, the -sc orientation around the C1—O1 bond (Φ) has not been considered in the selection of the starting structures. However, all three staggered orientations of the $\Psi_1$ and $\Psi_4$ dihedral angles have been assumed. Using this approach, 47 starting structures were generated for the optimisation of the geometry what led to 43 final structures. The relative energies and geometrical parameters of the relevant 6-31G* minima are summarised in Table 12. The relative energies of all the conformers except one are distributed in an interval of 19 kcal/mol.

Figure 8:
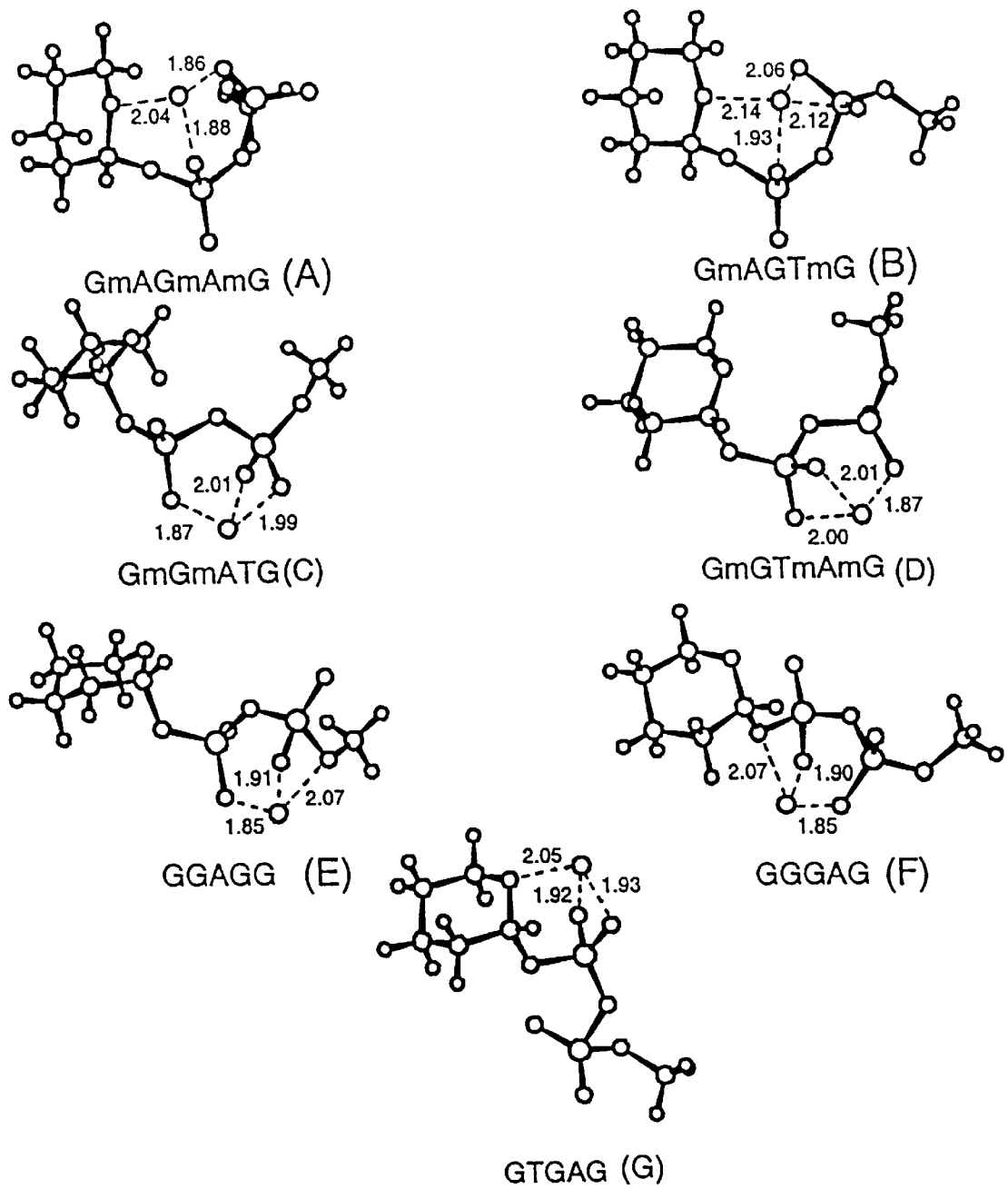
FIG. 8 is a representation of the seven $Mg^{2+}$ coordination patterns visible in the structures of the magnesium 2-O-methyldiphosphono-tetrahydropyran (4) calculated using the ab initio method at 6-31G* level. The letter illustrates the type of coordination referred in Table 2 and dashed lines connect magnesium with the coordinated oxygen atoms. Bond lengths are given in angstroms.

The structural analysis of the 43 minima revealed that they could be grouped into seven different patterns of the $Mg^{2+}$ . . . O coordination classified as A–G in Table 12. Each of the seven arrangements shown on FIG. 8 displays a particular conformation around the P—O—P segment (Ψ2, Ψ3). Four groups, namely A, E, F. and G, consist only of one conformer. Similarly to the magnesium dimethyl diphosphate complex, minima listed in Table 12 are characterised by the coordination of $Mg^{2+}$ with three oxygen atoms. Exceptions are minima belonging to the group B where four oxygen atoms coordinate $Mg^{2+}$. Surprisingly, interactions with the ring oxygen are preferred over those with the phosphoryl oxygen atoms. Since the arrangements A, B, and G involve an additional oxygen atom not present in the structure of the magnesium dimethyl diphosphate, these arrangements were not observed for that model. The most favourable conformation around the O—P—O bonds found for the magnesium dimethyldiphosphate complex, (ac, ap), corresponds to the arrangement C of 2. This arrangement is also the lowest energy conformation that does not involve the ring oxygen atom and therefore can be more directly related to the structure of the magnesium dimethyldiphosphate complex.

The two lowest energy arrangements, A and B, are characterised by interactions of the magnesium cation with the ring oxygen atom. In the lowest energy conformer (GmAGmAmG, group A), the $Mg^{2+}$ cation interacts with two additional oxygen atoms from both phosphate groups, whereas three additional oxygen atoms are involved in the conformers of group B. In spite of this, the relative energies of the group B conformers are 4–7 kcal/mol. The highest energy arrangement (60 kcal/mol), the group E, also involves interactions of the $Mg^{2+}$ cation with the ring oxygen atom, but in this case the coordination of the metal is with two oxygen atoms from the same nearest phosphate group. This conformation, however, exhibits a very unfavourable orientation of the phosphate group with respect to the pyranoid ring. For the groups C and D, three phosphoryl oxygen atoms coordinate the magnesium cation. A survey of all the minima of 4 reveals that the C—H . . . O hydrogen bond interactions, such as those observed in the anionic form, are not preserved in the presence of a counterion. Only few very weak CH . . . O hydrogen bond interactions can be seen in arrangements where the metal coordination involves interactions with the ring oxygen atom such as in patterns A, B and G. In the metal complex, interactions of the different oxygen atoms with the counterion appear to dominate clearly over the hydrogen bonding interactions.

Comparison of the calculated geometrical parameters for five conformers of 4 revealed that in the case of 4, the influence of the basis set on the conformer geometry is smaller compared to that calculated for 3. For example, the inclusion of diffuse functions into the basis set of the HF or B3LYP methods does not alter the bond length values. Similarly, variations of bond angles and torsional angles are rather small and do not exceed 2° and 5° respectively. Electron correlation effects, treated by means of DFT, results mainly in the lengthening of the C—O and P—O bonds from 0.02 Å to 0.04 Å. The coordination pattern and the location of the representative minima remain to be the same. The comparable relative energy issued from single point calculations of the different conformers implies also a similitude of the structures calculated using different basis sets and the HF and B3LYP methods. However, the relative energy of the conformers appears to be influenced by the electron correlation effects. Using the LMP2/6-31++G results as a benchmark, it is evident that the relative energy of the GmAGTmG and GGmGTG conformers decreases by 2–3 kcal/mol compared to the HF/6-31++G results (Table 13). These two structures are more compact than the three other conformers given in Table 13 what suggests that dispersion interactions are not adequately described in these complexes at HF level.

Components of the free energy of conformers in gas phase and two solvents are given in Table 14. It is clear that their influence on the conformational equilibrium for 4 is more pronounced than in the case of 3. Thermodynamic contributions stabilise the GmAGmAmG, GmGmATG, and GmGTmAmG conformers up to 6 kcal/mol. Though the absolute magnitudes of solvation energy are smaller compared to those of 3, they show a surprisingly large variability happening with the change of conformation. In cyclohexane, the solvation energy varies by 8 kcal/mol and in water as much as 28 kcal/mol. As a consequence, the conformational preference is shifted from GmAGmAmG in gas phase and cyclohexane to the GmGmATG conformer in water. Unfortunately no experimental data are available for a comparison. However, because the same approach predict correctly the pKa values for a large set of different molecules it is expected that the solvation energies are reasonably well predicted.

Figure 9:
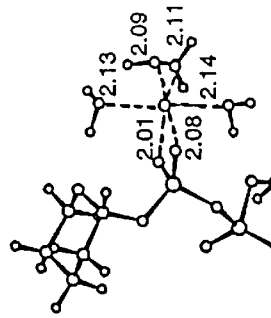
FIG. 9 is a representation of the eight clusters of the magnesium 2-O-methyldiphosphono-tetrahydropyran (4) with full first coordination shell of the metal calculated using the ab initio method at 6-31G*. Dashed lines connect magnesium with the coordinated oxygen atoms. Bond lengths are given in angstroms.
Figure 9:
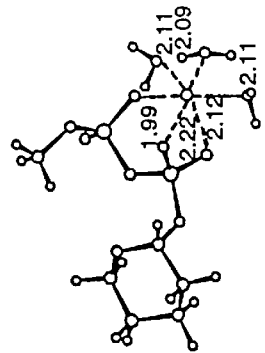
Figure 9:
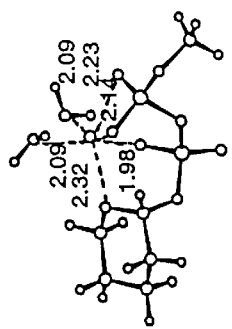
Figure 9:
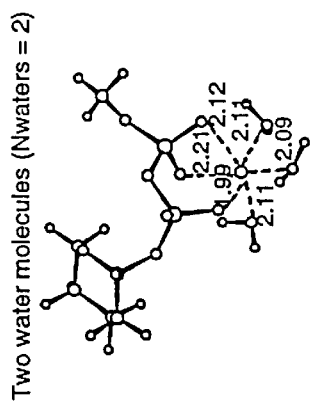
Figure 9:
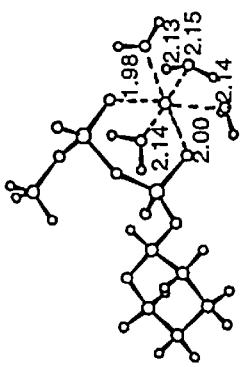
Figure 9:
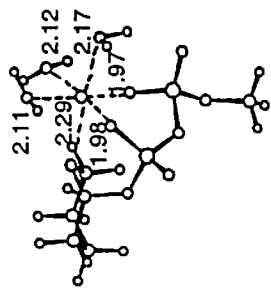

The interaction energy of a cation with the first-shell of ligands is stronger than the water-water or ligand-ligand interactions [66]. As a result, the first coordination shell of a cation in aqueous solution is well defined and metal cations may possibly have a full coordination shell. The most common first coordination shell of the $Mg^{2+}$ is a six-coordinated octahedron and the energetics of the interactions of the $Mg^{2+}$ with water, formamide and formate ligands has been studied using ab initio methods [67, 68]. From the coordination patterns observed for 4 (Table 12), it is clear that the oxygen atoms of the 2-O-methyldiphosphono-tetrahydropyran dianion (3) interacting with $Mg^{2+}$ only occupy a fraction of the binding sites accessible in the metal first coordination shell. Assuming the octahedral geometry for the $Mg^{2+}$, two to four binding sites are not occupied in conformers of 4. In order to evaluate the effect of the first coordination shell of $Mg^{2+}$ on the stability of 4, calculations were performed on several conformers of 4 with saturation of the first coordination shell. Though the size and the polarity of a ligand determines the magnitude of metal-ligand interactions, the binding ligands were restricted to water molecules. Based on the diphosphate-$Mg^{2+}$ coordination patterns described in Table 12, nine representative conformers were selected, namely GmAGmAmG (group A), GmAGTmG (group B), GGmGTG (group B), GmGmATG (group C), GmGTmAmG (group D), ATATmG (group C), GGAGG (group E), GGGAG (group F), and GTGAG (group G). The first coordination shell was filled out by two, three or four water molecules and these clusters were optimised at the HF/6-31G* level. The starting geometry for the clusters was based on the HF/6-3G* optimised structure of a given conformer with the oxygen atoms of the water molecules placed in the unoccupied sites of an octahedron. The results are summarised in Table 15 and the optimised structures are shown in FIG. 9. The comparison of Tables 12 and 15 shows clearly that the orientations about the sugar-diphosphate linkages in the clusters are changed compared to those observed in 2 conformers. The difference in some dihedral angles can be as large as 60°. These adjustments somehow allow the given cluster to adopt the best possible octahedral symmetry and thus maximise the binding. The clusters do not possess an ideal octahedral symmetry due to the different nature of the ligands and to some conformational constraints of the sugar-diphosphate linkages. Nevertheless, all clusters examined present four oxygen atoms (two from water molecules and two from 2) in nearly the same plane as $M^{2+}$. Such arrangement reduces the ligand-ligand repulsive interactions. The distance between the metal and water oxygens varies from 2.0 Å to 2.2 Å. From Table 15, it can be seen that estimated binding energies are roughly in the interval of 29–33 kcal/mol. The saturation of the unoccupied octahedral sites by water molecules results in the decrease of the relative energy of the conformers. These results imply that a magnesium complex with diphosphate functional group in nucleotide-sugars may adopt different conformations depending on the structural features imposed by the arrangement of the ligands in the first coordination shell of the metal.

Conclusions

The results of the conformational analyses of 3 and 4 clearly show that interactions of the diphosphate group with the $Mg^{2+}$ cation alter the conformational preferences around the diphosphate linkage. In the absence of the metal counterion, ($\Psi_2$, $\Psi_3$) torsion angles clearly prefer the (sc, ac) or (-sc, -ac) orientations but complexation by a metal cation changes this preference to (sc, -ac). As it has already been observed for the sodium 2-O-methylphosphono-tetrahydropyran, complexation with a metal counterion also changes the conformation about the anomeric C1—O1 linkage from the ac to sc orientation. The $\Psi_1$ dihedral angle does not remain inert to the effects of the complexation either. This demonstrates that interactions with a metal counterion induce some conformational changes in diphosphate linkages. These changes influence the overall 3D-shape adopted by nucleotide-sugars and therefore have consequences for their functions in biological processes. They also indicate that for an accurate overall description of the conformational behaviour of those compounds, a reliable estimate of thermodynamic and solvent contributions should be included into the calculations.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES (1) Varki, A. *Glycobiology* 1993, 3, 97–130.
(2) *Glycoproteins and Disease;* Montreuil, J.; Vliegenthart, J. F. G.; Schachter, H., Eds.; Elsevier: Amsterdam, 1995.
(3) Sinnott, M. L. *Chem. Rev.* 1990, 90, 1171–1202.
(4) Legler, G. *Carbohydr. Res.* 1993, 250, vii–xx.
(5) Withers, S. G.; Aebersold, R. *Protein Sci.* 1995, 4, 361–372.
(6) Khatra, B. S.; Herries, D. G.; Brew, K. *Eur. J. Biochem.* 1974, 44, 537–560.
(7) Tsopaknakis, A. D.; Herries, D. G. *Eur. J. Biochem.* 1978, 83, 179–188.
(8) Bendiak, B.; H. Schachter, H. *J. Biol. Chem.* 1987, 262, 5784–5790.
(9) Nishikawa, Y.; Pegg, W.; Paulsen, H. Schachter, H. *J. Biol. Chem.* 1988, 263, 7321–7322.
(10) Kim, S. C.; Singh, A. N.; Raushel, F. M. *J. Biol. Chem.* 1988, 263, 10151–10154.
(11) Kim, S. C.; Singh, A. N.; Raushel, F. M. *Arch. Biochem. Biophys.* 1988, 267, 54–58.
(12) Kearns, A. E.; Campbell, S. C.; Westley, J.; Schwartz, N. B. *Biochemistry* 1991, 30, 7477–7483.
(13) Ats, S.-C.; Lehmann, J.; Petry, S. *Carbohydr. Res.* 1992, 233, 125–139.
(14) Nakazawa, K.; Furukawa, K.; Narimatsu, K.; Kobata, A. *J. Biochem.* 1993, 113, 747–753.
(15) Yin, H.; Bennett, G.; Jones, J. P. *Chem. Biol. Interactions* 1994, 90, 47–58.
(16) Breuer, W.; Bause, E. *Eur. J. Biochem.* 1995, 228, 689–696.
(17) Strokopytov, B.; Penninga, D.; Rozeboom, H. J.; Kalk, K. H.; Dijkstra, B. W. *Biochemistry* 1995, 34, 2234–2240.
(18) Qiao, L.; Murray, B. W.; Shimazaki, M.; Schultz, J.; Wong, C. *J. Am. Chem. Soc.* 1996, 118, 7653–7662.
(19) Beyer, T. A.; Sadler, J. E.; Rearick, J. I.; Paulson, J. C.; Hill, R. L. *Adv. Enzymol.* 1981, 52, 23–175.
(20) *Glycoproteins;* Montreuil, J.; Vliegenthart, J. F. G.; Schachter, H.; Eds.; Elsevier: Amsterdam, 1995.
(21) *The Anomeric Effect, Origin and Consequences;* Szarek, W. A.; Horton, D.; Eds.; ACS Symposium Series 87; American Chemical Society: Washington, D.C., 1979.
(22) Kirby, A. J. In *The Anomeric Effect and Related Stereoelectronic Effects at Oxygen;* Springer-Verlag: Berlin, 1983.
(23) Deslongchamps, P. In *Stereoelectronic Effects in Organic Chemistry;* Pergamon: Oxford, U.K., 1983.
(24) Tvaroska, I.; Bleha, T. *Chem. Pap.* 1985, 39, 805–847.
(25) Tvaroska, I. In *Theoretical Chemistry of Biological Systems;* Naray-Szabo G., Ed.; Elsevier: Amsterdam, 1986, pp 283–348.

(26) Gorenstein, D. G. *Chem. Rev.* 1987, 87, 1047–177.
(27) Sinnott, M. L. *Adv. Phys. Org. Chem.* 1988, 24, 113–204.
(28) Tvaroska, I.; Bleha, T. *Adv. Carbohydr. Chem. Biochem.* 1989, 47, 45–123.
(29) Juaristi, E.; Cuevas, G. *Tetrahedron* 1992, 48, 5019–5087.
(30) *The Anomeric Effect and Associated Stereoelectronic Effects;* Thatcher, G. R. J., Ed.; ACS Symposium Series 539; American Chemical Society: Washington, D.C., 1992.
(31) Juaristi, E.; Cuevas, G. In *The Anomeric Effect;* CRC Press: Boca Raton, Fla.; 1994.
(32) Schneider, B.; Kabelac, M.; Hobza, P. *J. Am. Chem. Soc.* 1996, 118, 12207–12217.
(33) Florian, J.; Baumruk, V.; Strajbl, M.; Bednarova, L.; Stepanek, J. *J. Phys. Chem.* 1996, 100, 1559–1568.
(34) Tvaroska, I.; Carver, J. P. *J. Phys. Chem.* 1994, 98, 6452–6458.
(35) Tvaroska, I.; Carver, J. P. *J. Phys. Chem.* 1994, 98, 9477–9485.
(36) Tvaroska, I.; Carver, J. P. *J. Phys. Chem.* 1995, 99, 6234–6241.
(37) Tvaroska, I.; Carver, J. P. *J. Phys. Chem.* 1996, 100, 11305–11313.
(38) Tvaroska, I.; Carver, J. P. *J. Phys. Chem. B* 1997, 101, 2992–2999.
(39) Tvaroska, I.; Carver, J. P. *J. Molec. Struct., THEOCHEM,* 1997, 395–396, 1–15.
(40) *Turbomole 95.0 User Guide;* October 1995, San Diego: Biosym/MSI, 1995.
(41) Becke, A. D. *J. Chem. Phys.* 1993, 98, 5648–5652.
(42) Parr, R. G.; Yang, W. In *Density-Functional Theory of Atoms and Molecules;* Oxford University Press: New York, 1989.
(43) *InsightII 95.0 User Guide;* October 1995, San Diego: Biosym/MSI, 1995.
(44) *Discover 95.0 User Guide;* October 1995, San Diego: Biosym/MSI, 1995.
(45) Tvaroska, I.; Vaclavik, L. *Carbohydr. Res.* 1987, 160, 137–149.
(46) Dowd, M. K.; Reilly, P. J.; French, A. D. *J. Comput. Chem.* 1992, 13, 102–114.
(47) Lemieux, R. U.; Morgan, A. R *Can. J. Chem.* 1965, 43, 2205–2213.
(48) Jones, P. G.; Kirby, A. J. *J. Am. Chem. Soc.* 1984, 1068, 6207–6212.
(49) Bürgi, H.-B.; Dubler-Steudle, K. C. *J. Am. Chem. Soc.* 1988, 110, 7291–7299.
(50) J. W. Dennis, S. Laferte, C. Waghorne, M. L. Breitrnan and R. S. Kerbel, Science, 236 (1987) 582–585.
(51) B. Ma, C. Meredith and H. F. Schaefer, III, J. Phys. Chem., 98 (1994) 8216–8223.
(52) B. Ma, C. Meredith and H. F. Schaefer, III, J. Phys. Chem., 99 (1995) 3815–3822.
(53) M. E. Colvin, E. Evleth and Y. Akacem, J. Am. Chem. Soc., 117 (1995) 4357–4362.
(54) H. Saint-Martin, L. E. Ruiz-Vicent, A. Ramirez-Solis and I. Ortega-Blake, J. Am. Chem. Soc., 118 (1996) 12167–12273.
(55) G. R. Desiraju, Acc. Chem. Res., 24 (1991) 290–296.
(56) S. E. Barrows, F. J. Dulles, C. J. Cramer, A. D. French, and D. G. Truhlar, Carbohydr. Res., 276 (1995) 219–251.
(57) J. Andzelm, J. Baker, A. Scheiner, and M. Wrinn, Int. J. Quantum Chem. 56 (1995) 733–746.
(58) F. H. Allen, J. E. Davies, J. J. Galloy, O. Johnson, O. Kennard, C. F. Macrae, E. M. Mitchell, G. F. Mitchell, J. M. Smith, and D. G. Watson, J.Chem. Inf. Comput. Sci. 31 (1991) 187–204.
(59) J. J. Pavelites, J. Gao, P. A. Bash and A. D. Mackerell, Jr., J. Comput. Chem. 18 (1997) 221–239.
(60) Murphy, R. B.; Beachy, M. D.; Friesner, R. A.; Ringnalda, M. N. *J. Chem. Phys.* 1995, 103, 1481–14.
(61) Tannor, D. J.; Marten, B.; Murphy, R.; Friesner, R. A.; Sitkoff, D.; Nicholls, A.; Ringnalda, M.; Goddard III, W. A.; Honig, B. *J. Am. Chem. Soc.* 1994, 116, 11875–1187
(62) Steiner, T.; Saenger, W. *J. Am. Chem. Soc.* 1992, 114, 10146–10154.
(63) Aakeroy, C. B.; Seddon, K. R. *Chem. Soc. Rev.* 1993, 397–407.
(64) Tvaroska, I.; Bleha, T. *Adv. Carbohydr. Chem. Biochem.* 1989, 47, 45–123.
(65) Colvin, M. E.; Evleth, E.; Akacem, Y. *J. Am. Chem. Soc.* 1995, 117, 4357–4362.
(66) Lehn, J.-M. *Structure and Bonding;* Dunitz, J. D., Hemmerich, P., Ibers, J. A., Jorgensen, C. K., Neilands, J. B., Reinin, D. and Wiliams, R. J. P., Ed.; Springer Verlag, Inc.: New York, 1973; Vol. 16, pp 1–69
(67) Deerfield, I., D. W. ; Lapadat, M. A.; Spremulli, L. L.; Hiskey, R. G.; Pedersen, L. G. *J. Biomol. Struct. & Dynamics* 1989, 6, 1077–1091.
(68) Krauss, M., Stevens, W. J. J. Am. Chem Soc. 1990, 112, 1460–1466.

TABLE 1

*Ab Initio* Relative Energy, Vibrational Correction, and Free Energy (kcal/mol), and the Position of Conformational Minima of the 2-Methylphosphono-tetrahydropyran Anion (1).

| Conformer | Φ | $\Psi_1$ | $\Psi_2$ | ΔE g-31G* | ΔE tzp//6-31G* | Δcorr 6-31G* | $\Delta(\Delta G_{298})$ 6-31G* |
|---|---|---|---|---|---|---|---|
| GGG | 66.9 | 50.5 | 80.0 | 4.07 | 4.44 | 0.32 | 3.30 |
| GGMG | 60.6 | 34.0 | −112.9 | 3.63 | 4.42 | 1.36 | 3.91 |
| GMGG | 89.7 | −90.0 | 97.7 | 1.40 | 1.78 | 0.78 | 1.09 |
| GMGT | 87.4 | −88.5 | 174.8 | 2.26 | 2.28 | 0.01 | 1.17 |
| GTG | 72.6 | 142.5 | 75.8 | 1.71 | 2.06 | 0.65 | 1.27 |

TABLE 1-continued

*Ab Initio* Relative Energy, Vibrational Correction, and Free Energy (kcal/mol), and the Position of Conformational Minima of the 2-Methylphosphono-tetrahydropyran Anion (1).

| Conformer | Φ | Ψ$_1$ | Ψ$_2$ | ΔE g-31G* | ΔE tzp//6-31G* | Δcorr 6-31G* | Δ(ΔG$_{298}$) 6-31G* |
|---|---|---|---|---|---|---|---|
| GTMG | 69.6 | 149.2 | −72.9 | 1.40 | 1.83 | 1.08 | 1.39 |
| GTT | 75.2 | 141.1 | 163.5 | 2.78 | 3.24 | 0.00[c] | 1.68 |
| MGGG | −56.8 | 78.1 | 67.0 | 7.31 | 7.33 | 0.86 | 7.07 |
| MGGT | −59.0 | 85.9 | 172.2 | 9.38 | 9.46 | 0.33 | 8.62 |
| MGMGMG | −100.6 | −70.6 | −75.0 | 6.66 | 6.97 | 1.34 | 6.91 |
| MGMGT | −100.7 | −69.0 | −177.8 | 7.68 | 7.97 | 0.82 | 7.41 |
| TGG | 160.3 | 97.4 | 81.7 | 1.31 | 1.52 | 1.13 | 1.35 |
| TGT | 159.1 | 95.2 | 176.6 | 2.02 | 2.24 | 0.44 | 1.37 |
| TMGMG | 142.4 | −73.6 | −70.8 | 0.00[a] | 0.00[b] | 1.09 | 0.00[d] |
| TMGT | 145.9 | −78.8 | 171.4 | 1.77 | 1.76 | 0.37 | 1.05 |
| TTG | 170.3 | −148.0 | 70.4 | 0.85 | 1.11 | 0.83 | 0.59 |

[a]E = −595737.37 kcal/mol; [b]E = −595880.04 kcal/mol; [c]Δcorr = ZPE + ΔH$_{298}$ − TΔS = 236.0 kcal/mol; [d]ΔG$_{298}$ = −595500.28 kcal/mol.

TABLE 2

Comparison of the *ab Initio* Energies and Relative Energies (kcal/mol) of Selected Conformers of the 2-O-Methylphosphono-tetrahydropyran anion (1) Calculated by Different Methods.

| Geometry | energy | TMGMG | TTG | GMGG | GTMG |
|---|---|---|---|---|---|
| 6-31G* | 6-31G* | −595737.373 | 0.85 | 1.40 | 1.40 |
|  | tzp | −595839.780 | 1.03 | 1.89 | 1.95 |
|  | ACM/6-31G* | −595156.359 | 0.66 | 0.95 | 0.94 |
| ACM/6-31G* | ACM/6-31G* | −598159.744 | 0.64 | 0.61 | 0.87 |
|  | ACM/tzp | −598315.372 | 0.91 | 1.00 | 1.44 |
| ACM/tzp | ACM/tzp | −598315.636 | 0.92 | 1.02 | 1.38 |

TABLE 3

*Ab Initio* Calculated Geometrical Parameters of the 2-O-Methylphosphono-tetrahydropyran anion (1) at the 6-31G* level.[a]

| Conformer | C5-O5 | O5-C1 | C1-O1 | O1-P | P-O4 | P-O2 | O5-C1-O1 | C1-O1-P | O1-P-O4 | P-O4-C | O2-P-O3 |
|---|---|---|---|---|---|---|---|---|---|---|---|
| GGG | 1.403 | 1.395 | 1.380 | 1.658 | 1.638 | 1.471 | 114.0 | 125.5 | 99.1 | 118.8 | 124.2 |
| GGMG | 1.408 | 1.399 | 1.377 | 1.656 | 1.636 | 1.466 | 113.6 | 125.9 | 99.3 | 120.0 | 123.3 |
| GMGG | 1.403 | 1.408 | 1.377 | 1.657 | 1.632 | 1.476 | 111.8 | 123.2 | 100.7 | 120.3 | 124.8 |
| GMGT | 1.402 | 1.401 | 1.382 | 1.641 | 1.639 | 1.475 | 112.2 | 122.6 | 97.1 | 116.9 | 122.8 |
| GTG | 1.404 | 1.400 | 1.380 | 1.660 | 1.630 | 1.468 | 112.3 | 121.6 | 97.1 | 119.4 | 124.5 |
| GTMG | 1.405 | 1.399 | 1.380 | 1.661 | 1.629 | 1.475 | 112.5 | 121.4 | 96.7 | 119.4 | 124.4 |
| GTT | 1.404 | 1.400 | 1.381 | 1.644 | 1.637 | 1.474 | 112.1 | 121.7 | 94.5 | 117.1 | 122.6 |
| MGGG | 1.412 | 1.395 | 1.386 | 1.644 | 1.632 | 1.469 | 114.8 | 133.3 | 100.1 | 119.2 | 124.1 |
| MGGT | 1.411 | 1.392 | 1.388 | 1.626 | 1.639 | 1.469 | 115.0 | 134.4 | 97.4 | 116.8 | 121.8 |
| MGMGMG | 1.410 | 1.395 | 1.386 | 1.642 | 1.638 | 1.468 | 111.9 | 134.6 | 100.0 | 118.6 | 124.0 |
| MGMGT | 1.410 | 1.395 | 1.388 | 1.625 | 1.645 | 1.468 | 111.7 | 135.5 | 97.5 | 116.7 | 121.9 |
| TGG | 1.401 | 1.401 | 1.389 | 1.650 | 1.638 | 1.470 | 108.5 | 121.5 | 99.5 | 119.0 | 125.1 |
| TGT | 1.403 | 1.399 | 1.390 | 1.634 | 1.646 | 1.476 | 108.4 | 122.1 | 96.6 | 116.8 | 123.1 |
| TMGMG | 1.402 | 1.403 | 1.386 | 1.652 | 1.633 | 1.471 | 109.1 | 120.2 | 99.3 | 118.9 | 125.0 |
| TMGT | 1.403 | 1.400 | 1.389 | 1.634 | 1.640 | 1.468 | 109.1 | 120.9 | 96.9 | 117.2 | 122.9 |
| TTG | 1.404 | 1.401 | 1.387 | 1.654 | 1.623 | 1.468 | 108.2 | 121.0 | 97.4 | 119.2 | 123.3 |

[a]Lengths in angstroms, angles in degrees.

TABLE 4

*Ab Initio* Relative Energy, Vibrational Correction, and Free Energy (kcal/mol), and the Position (torsion angles in degrees) of Conformational Minima of the Sodium 2-Methylphosphono-tetrahydropyran (2)

| conformer | φ | Ψ$_1$ | Ψ$_2$ | ΔE 6-31G* | ΔE tzp//6-31G* | Δcorr 6-31G* | Δ(ΔG$_{298}$) 6-31G* |
|---|---|---|---|---|---|---|---|
| GGG | 67.5 | 49.5 | 76.0 | 7.01 | 6.56 | 1.19 | 4.68 |
| GGmG | 60.9 | 32.3 | −109.0 | 6.24 | 6.04 | 2.14 | 4.87 |
| GGT | 61.0 | 37.2 | −160.1 | 6.60 | 5.94 | 1.52 | 4.61 |
| GmGG | 83.5 | −82.3 | 94.5 | 5.46 | 5.04 | 1.83 | 3.78 |
| GmGmG | 86.7 | −88.9 | −76.8 | 5.23 | 5.18 | 3.67 | 5.38 |
| GmGT | 81.2 | −80.9 | 174.6 | 6.08 | 5.19 | 1.22 | 3.79 |
| GTG | 58.1 | 153.2 | 74.9 | 0.39 | 0.36 | 3.22 | 0.09 |
| GTmG | 57.5 | 156.7 | −68.3 | 0.00[a] | 0.00[b] | 3.51 | 0.00[d] |
| GTT | 58.4 | 153.7 | 170.4 | 0.85 | 0.78 | 2.96 | 0.30 |
| mGGG | −76.9 | 74.5 | 62.9 | 12.05 | 11.22 | 3.97 | 12.51 |
| mGmGmG | −101.4 | −64.1 | −74.0 | 11.49 | 10.83 | 1.99 | 9.97 |
| mGmGT | −100.7 | −69.0 | −177.8 | 12.15 | 11.23 | 2.01 | 10.64 |
| TGT | 121.0 | 85.3 | −179.2 | 5.92 | 4.84 | 0.65 | 3.06 |
| TmGmG | 128.2 | −62.8 | −63.4 | 4.84 | 4.11 | 1.82 | 3.15 |
| TmGT | 134.2 | −64.9 | 174.1 | 6.89 | 5.83 | 0.98 | 4.36 |
| TTG | 150.0 | −134.9 | 58.9 | 6.44 | 5.73 | 3.80 | 6.72 |
| TTmG | 148.3 | −151.7 | −66.1 | 7.21 | 6.37 | 0.00[a] | 3.69 |

[a]E = −697 326.84 kcal/mol.
[b]E = −697 467.91 kcal/mol.
[c]Δcorr = ZPE + ΔK$_{298}$ − TΔS = 236.0 kcal/mol.
[d]ΔG$_{298}$ = −697 087.33 kcal/mol.

TABLE 5

Comparison of the *ab Initio* Energies and Relative Energies (kcal/mol) of Selected Conformers of the Sodium 2-O-Methylphosphono-tetrahydropyran (2) Calculated by Different Methods.

| Geometry | energy | | GTMG | GTG | TMGMG | TTG |
|---|---|---|---|---|---|---|
| 6-31G* | 6-31G* | −697326.843 | 0.39 | 4.84 | 6.44 |
| | tzp | −697467.905 | 0.36 | 4.11 | 5.73 |
| | ACM/6-31G* | −699988.868 | 0.51 | 5.80 | 7.15 |
| ACM/6-31G* | ACM/6-31G* | −699991.974 | 0.52 | 5.94 | 6.52 |
| | ACM/tzp | −700143.883 | 0.55 | 5.34 | 6.11 |
| ACM/tzp | ACM/tzp | −700144.152 | 0.42 | 5.36 | 6.49 |

TABLE 7

Comparison of the Relative Energies (kcal/mol) Calculated by MNDO and Different Molecular Mechanics Methods for the 2-Methylphosphono-tetrahydropyran Anion (1).

| Conformer | MNDO | CVFF (ε = 1) | CVFF (ε = 4) | AMBER (ε = 1) | AMBER (ε = 4) |
|---|---|---|---|---|---|
| GGG | 0.69 | 4.73 | 0.88 | 6.93 | 2.62 |
| GGMG | 1.10 | 4.51 | 1.87 | 6.39 | 1.75 |
| GGT | — | 3.00 | 0.63 | 6.14 | 1.63 |
| GMGG | — | 2.60 | 1.34 | 2.85 | 0.85 |
| GMGMG | — | 2.18 | 0.46 | — | 0.43 |
| GMGT | — | 1.14 | 0.00 | 2.87 | 0.72 |

TABLE 6

*Ab Initio* Calculated Geometrical Parameters of the Sodium 2-O-Methylphosphono-tetrahydropyran (2) at the 6-31G* level.[a]

| Conformer | C5-O5 | O5-C1 | C1-O1 | O1-P | P-O4 | P-O2 | O5-C1-O1 | C1-O1-P | O1-P-O4 | P-O4-C | P-O2-Na |
|---|---|---|---|---|---|---|---|---|---|---|---|
| GGG | 1.410 | 1.379 | 1.411 | 1.603 | 1.597 | 1.493 | 112.2 | 125.4 | 103.1 | 120.3 | 99.3 |
| GGMG | 1.414 | 1.385 | 1.406 | 1.603 | 1.593 | 1.500 | 111.9 | 125.4 | 103.0 | 122.6 | 90.2 |
| GMGG | 1.413 | 1.387 | 1.406 | 1.604 | 1.591 | 1.487 | 111.1 | 124.3 | 105.1 | 122.7 | 89.8 |
| GMGT | 1.412 | 1.380 | 1.414 | 1.591 | 1.593 | 1.493 | 111.4 | 123.7 | 101.0 | 120.1 | 90.3 |
| GTG | 1.424 | 1.413 | 1.395 | 1.633 | 1.579 | 1.486 | 110.8 | 117.6 | 101.3 | 121.3 | 86.6 |
| GTMG | 1.426 | 1.412 | 1.395 | 1.633 | 1.579 | 1.493 | 110.8 | 117.6 | 101.0 | 121.3 | 86.0 |
| GTT | 1.425 | 1.413 | 1.396 | 1.619 | 1.583 | 1.493 | 110.7 | 117.5 | 98.3 | 119.8 | 85.7 |
| MGGG | 1.415 | 1.380 | 1.417 | 1.589 | 1.595 | 1.493 | 112.3 | 136.4 | 104.3 | 120.5 | 89.1 |
| MGMGMG | 1.414 | 1.378 | 1.418 | 1.589 | 1.598 | 1.492 | 110.7 | 137.2 | 104.3 | 120.3 | 89.9 |
| MGMGT | 1.414 | 1.378 | 1.419 | 1.577 | 1.599 | 1.493 | 110.6 | 138.4 | 101.4 | 119.8 | 90.8 |
| TGT | 1.411 | 1.382 | 1.416 | 1.587 | 1.598 | 1.492 | 109.1 | 123.9 | 100.0 | 120.0 | 89.8 |
| TMGMG | 1.412 | 1.382 | 1.415 | 1.600 | 1.593 | 1.492 | 108.9 | 121.9 | 103.5 | 120.9 | 89.2 |
| TMGT | 1.411 | 1.378 | 1.418 | 1.586 | 1.595 | 1.500 | 108.9 | 123.4 | 100.4 | 120.4 | 89.7 |
| TTG | 1.412 | 1.380 | 1.413 | 1.598 | 1.588 | 1.489 | 108.1 | 125.1 | 101.1 | 120.8 | 90.2 |

[a]Lengths in angstroms, angles in degrees.

TABLE 7-continued

Comparison of the Relative Energies (kcal/mol) Calculated by MNDO and Different Molecular Mechanics Methods for the 2-Methylphosphono-tetrahydropyran Anion (1).

| Conformer | MNDO | CVFF ($\epsilon = 1$) | CVFF ($\epsilon = 4$) | AMBER ($\epsilon = 1$) | AMBER ($\epsilon = 4$) |
|---|---|---|---|---|---|
| GTG | 1.23 | — | 0.57 | 4.30 | 1.16 |
| GTMG | 1.44 | — | 0.70 | 4.56 | 1.26 |
| GTT | — | — | 0.53 | 4.26 | 2.01 |
| MGGG | 4.80 | 7.79 | 5.19 | 11.56 | 8.31 |
| MGGT | — | 7.59 | 6.34 | 12.36 | 9.38 |
| MGMGMG | 5.18 | 9.76 | 6.97 | 12.42 | 8.59 |
| MGMGT | — | 8.28 | 6.53 | 12.10 | 9.27 |
| MGTG | 6.18 | 8.05 | 6.66 | — | — |
| MGTMG | — | 7.80 | 6.55 | — | — |
| MGTT | — | 6.93 | 6.49 | — | — |
| TGG | — | 2.67 | 1.25 | 0.51 | 0.00 |
| TGT | — | 1.65 | 1.08 | 0.66 | 0.78 |
| TMGG | 1.41 | — | — | — | — |
| TMGMG | 0.00 | 1.91 | 0.87 | 0.45 | 0.24 |
| TMGT | — | 1.30 | 0.95 | 0.92 | 1.24 |
| TTG | 1.35 | 0.86 | 0.80 | 0.00 | 0.54 |
| TTMG | — | 1.01 | 0.78 | 0.09 | 0.56 |
| TTT | — | 0.00 | 0.75 | 0.27 | 1.44 |

TABLE 8

Comparison of the Relative Energies (kcal/mol) Calculated by MNDO and Different Molecular Mechanics Methods for the Sodium 2-Methyl-phosphono-tetrahydropyran (2).

| Conformer | MNDO | CVFF ($\epsilon = 1$) | CVFF ($\epsilon = 4$) | AMBER ($\epsilon = 1$) | AMBER ($\epsilon = 4$) |
|---|---|---|---|---|---|
| GGG | — | 5.96 | 1.89 | 6.76 | 0.34 |
| GGMG | 3.04 | 5.75 | 2.93 | 6.48 | 1.37 |
| GGT | — | 6.14 | 2.14 | 8.35 | 1.80 |
| GMGM | 2.08 | 5.24 | 2.72 | 4.19 | 0.76 |
| GMGMG | 0.92 | 4.88 | 1.85 | 4.27 | 0.21 |
| GMGT | — | 5.65 | 1.93 | 6.09 | 1.13 |
| GTG | 0.00 | 0.06 | 0.00 | 0.00 | 0.00 |
| GTMG | 0.77 | 0.20 | 0.06 | 0.22 | 0.06 |
| GTT | — | 0.00 | 0.16 | 1.18 | 1.22 |
| MGGG | 5.65 | 9.18 | 6.35 | 12.53 | 8.14 |
| MGGMG | — | — | — | 17.20 | 11.66 |
| MGGT | 8.05 | — | — | 16.12 | 9.99 |
| MGMGMG | 5.63 | 10.40 | — | 13.04 | 8.25 |
| MGMGT | — | 10.73 | 6.90 | 14.95 | 9.60 |
| MGTG | — | 13.85 | 8.34 | — | 9.75 |
| MGTMG | — | 13.61 | 8.24 | — | — |
| MGTT | — | 15.70 | 8.65 | — | — |
| TGG | — | 5.57 | 2.57 | 3.23 | 0.02 |
| TGMG | — | — | — | 6.51 | 2.49 |
| TGT | — | 6.47 | 2.87 | 5.44 | 1.38 |
| TMGG | — | 8.50 | 4.54 | 5.68 | 1.34 |
| TMGMG | — | 5.81 | 2.49 | 4.07 | 0.43 |
| TMGT | — | 7.33 | 3.14 | 7.18 | 2.18 |
| TTG | — | 7.01 | 2.97 | 6.50 | 1.54 |
| TTMG | — | 7.15 | 2.94 | — | 1.56 |
| TTT | — | 8.84 | 3.62 | 10.24 | 3.40 |

TABLE 9

*Ab Initio* Relative Energy (kcal/mol), and Position of Conformational Minima of the 2-O-methyldiphosphono-tetrahydropyran dianion (1) Calculated at the 6-31G* Level

| Conformer | $\phi$ | $\Psi_1$ | $\Psi_2$ | $\Psi_3$ | $\Psi_4$ | $\Delta E$ |
|---|---|---|---|---|---|---|
| AAmGmAG | 104.1 | 107.7 | −59.9 | −101.8 | 73.3 | 0.00[a] |
| AGGAmG | 153.5 | 83.9 | 63.7 | 93.1 | −76.8 | 0.73 |
| AAGGG | 135.4 | 91.3 | 46.8 | 18.3 | 75.6 | 1.24 |
| AAmGmGmG | 108.9 | 101.6 | −45.2 | −38.5 | −70.5 | 1.28 |
| TmGAGmG | 173.3 | −55.8 | 90.8 | 74.1 | −87.1 | 1.77 |
| AAmGAmG | 97.2 | 110.3 | −60.1 | 135.6 | −66.2 | 2.25 |
| TAmAmGmG | 162.6 | 91.9 | −134.4 | −47.5 | −62.7 | 2.61 |
| TGTGmA | 162.4 | 89.1 | −150.4 | 72.6 | −92.7 | 2.69 |
| TGTmAG | 159.5 | 83.3 | −172.4 | −111.2 | 70.5 | 2.76 |
| GmAmGmGG | 88.4 | −92.2 | −69.8 | −74.1 | 88.7 | 2.80 |
| TmGAGG | 176.5 | −55.6 | 90.0 | 54.8 | 53.8 | 3.02 |
| TmGmGmGG | −176.3 | −34.5 | −71.5 | −67.2 | 87.2 | 3.28 |
| TmGmGmCmG | −175.8 | −44.8 | −57.0 | −27.2 | −71.7 | 3.39 |
| TmmGGmAG | 159.2 | −89.3 | 72.5 | −133.4 | 68.1 | 3.47 |
| AmAmGmGmG | 90.2 | −108.1 | −59.1 | −46.7 | −62.8 | 3.50 |
| AAmATG | 137.6 | 94.6 | −111.4 | −177.7 | 66.3 | 3.58 |
| GTGAmG | 72.1 | 158.7 | 58.4 | 96.9 | −78.4 | 3.79 |
| TmGAAT | 173.6 | −54.5 | 100.5 | 100.5 | −169.7 | 3.97 |
| TmGATmG | 173.9 | −54.9 | 99.7 | −168.5 | −66.7 | 3.98 |
| AmAGGG | 103.6 | −136.6 | 35.1 | 47.0 | 64.0 | 4.18 |
| TmGTAmG | 156.9 | −59.9 | −175.9 | 103.7 | −73.9 | 4.52 |
| AAmGAT | 98.8 | 106.6 | −48.9 | 108.4 | 179.1 | 4.63 |
| AmAmGTmG | 100.7 | −91.5 | −70.9 | 163.9 | −68.9 | 5.04 |
| TAGTG | 157.2 | 106.3 | 63.5 | 179.9 | 64.5 | 5.04 |
| TTAmGA | 173.5 | −153.5 | 100.1 | −42.6 | 95.2 | 5.34 |
| GmATmAG | 73.8 | −92.7 | 157.4 | −91.7 | 77.2 | 5.57 |
| TGGmAT | 150.8 | 85.7 | 69.4 | −143.4 | −179.5 | 5.59 |
| GTGmAG | 69.4 | 159.4 | 58.8 | −132.5 | 68.0 | 5.75 |
| TmGmAGG | 151.2 | −65.0 | −120.4 | 59.0 | 65.0 | 5.96 |
| GmATmGmG | 73.5 | −90.8 | 163.7 | −46.4 | −64.0 | 6.11 |
| TTTGG | 173.3 | −152.1 | 167.0 | 33.2 | 71.7 | 6.27 |
| TmAAmGmG | 174.4 | −149.2 | 103.2 | −50.3 | −71.7 | 6.28 |
| TmGATT | 175.3 | −57.8 | 95.0 | −161.2 | −180.0 | 6.50 |
| GATGG | 75.4 | 142.2 | 158.7 | 35.8 | 68.9 | 6.74 |
| TATAG | 161.4 | 97.4 | −176.2 | 99.4 | 82.8 | 7.14 |
| GmAmGTT | 89.5 | −91.0 | −71.5 | 151.9 | 177.2 | 7.82 |
| TmGmGAT | −174.8 | −33.7 | −68.9 | 145.0 | −178.3 | 8.50 |

[a] E = −950 507.26 kcal/mol.

TABLE 10

Comparison of the *ab Initio* Relative Energies (kcal/mol) of Selected 2-O-Methyldiphosphono-tetrahydropyran dianion (1) Conformers calculated by Different methods

| | Method | | Conformer | | | | |
|---|---|---|---|---|---|---|---|
| | Energy | Geometry | AAmGmAG | AGGAmG | AAGGG | AAmGmGmG | TmGAGmG |
| HF | 6-31G* | 6-31G* | 0.00 | 0.73 | 1.24 | 1.28 | 1.77 |
| HF | 6-31++G** | 6-31G* | 0.00 | 0.54 | 0.29 | 0.36 | 1.90 |
| HF | cc-pVTZ(-f)++ | 6-31G* | 0.00 | 0.54 | 0.43 | 1.00 | 1.88 |
| HF | 6-31++G** | 6-31++G** | 0.00 | 0.51 | 0.51 | 1.34 | 2.00 |
| HF | cc-pVTZ(-f)++ | 6-31++G** | 0.00 | 0.32 | 0.41 | 1.11 | 1.90 |
| DFT/B3LYP | 6-31G** | 6-31G** | 0.00 | 0.67 | 0.86 | 0.70 | 1.26 |
| DFT/B3LYP | 6-31++G** | 6-31G** | 0.00 | 0.73 | 0.64 | 0.49 | 1.67 |
| DFT/B3LYP | cc-pVTZ(-f)++ | 6-31G** | 0.00 | 0.65 | 0.49 | 0.59 | 1.83 |
| DFT/B3LYP | 6-31++G** | 6-31++G** | 0.00 | 0.73 | 0.64 | 0.49 | 1.67 |
| DFT/B3LYP | cc-pVTZ(-f)++ | 6-31++G** | 0.00 | 0.51 | 0.44 | 0.77 | 1.67 |
| LMP2 | cc-pVTZ(-f)++ | 6-31G* | 0.30 | 0.00 | 0.08 | 0.52 | 1.51 |
| LMP2 | cc-pVTZ(-f)++ | 6-31++G** | 0.14 | 0.00 | 0.36 | 0.68 | 1.75 |

TABLE 11

Summary of Corrections to the Calculated Free Energy Differences (kcal/mol) for the AamGmAG, AGGAmG, AAGGG, AAmGmGmG, and TmGAGmG conformers of 2-O-Methyldiphosphono-tetrahydropyran dianion (1) in Gas Phase, Cyclohexane and Water at 298K

| | Method | AAmGmAG | AGGAmG | AAGGG | AAmGmGmG | TmGAGmG |
|---|---|---|---|---|---|---|
| ZPE | HF/6-31G* | 121.28 | 120.64 | 122.17 | 120.86 | 120.49 |
| $\Delta G_{vib,rot}$ | HF/6-31G* | −28.20 | −28.11 | −28.10 | −28.18 | −27.86 |
| $\Delta G(Cyclohexane)_{Solv}$ | B3LYP/6-31G** | −89.84 | −90.05 | −88.11 | −89.82 | −88.57 |
| $\Delta G(Water)_{Solv}$ | B3LYP6-31G** | −204.14 | −205.44 | −200.81 | −203.71 | −202.74 |
| $\Delta E$ | HF/cc-pVTZ(-f)++//6-31++G** | 0.00 | 0.32 | 0.41 | 1.11 | 1.90 |
| $\Delta G_{gas}$ | | 0.24 | 0.00 | 1.63 | 0.94 | 1.04 |
| $\Delta G_{cyclohexane}$ | | 0.40 | 0.00 | 2.09 | 0.76 | 1.26 |
| $\Delta G_{water}$ | | 1.49 | 0.00 | 4.78 | 2.16 | 2.48 |
| $\Delta E$ | B3LYP/cc-pVTZ(-f)++//6-31++G** | 0.00 | 0.51 | 0.44 | 0.77 | 1.67 |
| $\Delta G_{gas}$ | | 0.05 | 0.00 | 1.47 | 0.41 | 1.25 |
| $\Delta G_{Cyclohexane}$ | | 0.20 | 0.00 | 1.94 | 0.23 | 1.48 |
| $\Delta G_{water}$ | | 1.30 | 0.00 | 4.63 | 1.73 | 2.70 |
| $\Delta E$ | LMP2/cc-pVTZ(-f)++//6-31++G** | 0.14 | 0.00 | 0.36 | 0.68 | 1.75 |
| $\Delta G_{gas}$ | | 0.69 | 0.00 | 1.90 | 0.84 | 1.85 |
| $\Delta G_{cyclohexane}$ | | 0.85 | 0.00 | 2.36 | 0.65 | 2.07 |
| $\Delta G_{water}$ | | 1.94 | 0.00 | 5.05 | 2.15 | 3.28 |

TABLE 12

*Ab Initio* Relative Energy (kcal/mol) and the Position of Conformational Minima of the Magnesium 2-O-methyldiphosphono-tetrahydropyran Complex (2) at the 6-31G* Level

| Conformer | φ | $\Psi_1$ | $\Psi_2$ | $\Psi_3$ | $\Psi_4$ | $Mg^{2+}$ coordination | $\Delta E$ |
|---|---|---|---|---|---|---|---|
| GmAGmAmG | 87.3 | −133.7 | 61.7 | −91.9 | −75.5 | A | 0.00[a] |
| GmAGTmG | 86.4 | −131.5 | 78.1 | −178.9 | −59.5 | B | 4.13 |
| GmGTG | 87.1 | −132.4 | 77.9 | 178.6 | 55.1 | B | 4.56 |
| GGmGTG | 48.2 | 64.4 | −87.9 | −178.2 | 58.3 | B | 4.92 |
| GGmGTmG | 43.7 | 68.3 | −85.6 | −177.5 | −56.1 | B | 5.54 |
| GmAGTT | 86.7 | −132.4 | 78.0 | −179.9 | −177.7 | B | 5.67 |
| GGmGTT | 46.1 | 66.7 | −86.6 | −177.9 | 175.1 | B | 6.36 |
| GmGmATG | 78.5 | −83.9 | −105.3 | 176.2 | 48.0 | C | 9.67 |
| GmGTmAmG | 68.9 | −79.4 | 174.5 | −96.8 | −69.7 | D | 9.81 |
| AmGmATmG | 92.3 | −78.7 | −97.3 | 174.1 | −53.2 | C | 9.86 |
| GGTmAmG | 66.4 | 42.5 | 174.1 | −103.2 | −79.5 | D | 10.21 |
| GGmATG | 70.0 | 60.9 | −112.0 | −178.1 | 60.7 | C | 10.31 |
| AATmAmG | 118.6 | 100.1 | 177.3 | −103.5 | −77.7 | D | 10.61 |
| AGTmAmG | 144.7 | 86.9 | −179.6 | −108.9 | −82.5 | D | 10.64 |
| GmGTAG | 84.9 | −82.6 | −179.8 | 109.7 | 84.7 | D | 10.72 |
| AmGmATG | 141.9 | −70.6 | −109.7 | 179.8 | 58.8 | C | 10.93 |
| AATAG | 132.8 | 91.0 | 179.0 | 109.8 | 79.9 | D | 11.16 |
| GGmATmG | 69.1 | 60.9 | −111.3 | −176.7 | −58.4 | C | 11.28 |
| GmGmATT | 85.3 | −85.5 | −104.4 | 177.8 | 172.2 | C | 11.31 |
| GGATmG | 51.0 | 40.5 | 111.0 | 179.1 | −56.2 | C | 11.37 |
| GmGTmAG | 65.5 | −86.3 | −172.0 | −125.6 | 62.6 | D | 11.42 |

TABLE 12-continued

*Ab Initio* Relative Energy (kcal/mol) and the Position of Conformational Minima of the Magnesium 2-O-methyldiphosphono-tetrahydropyran Complex (2) at the 6-31G* Level

| Conformer | φ | $\Psi_1$ | $\Psi_2$ | $\Psi_3$ | $\Psi_4$ | $Mg^{2+}$ coordination | ΔE |
|---|---|---|---|---|---|---|---|
| ATATmG | 108.1 | 171.4 | 109.7 | −177.8 | −51.9 | C | 11.52 |
| GGTmAmA | 68.0 | 40.6 | 178.9 | −113.7 | −148.3 | D | 11.57 |
| GGTAmG | 66.1 | 37.8 | 169.8 | 126.0 | −64.3 | D | 11.58 |
| GmGTmAT | 71.0 | −84.6 | −178.0 | −112.7 | −161.7 | D | 11.60 |
| AmGTmAmG | 145.0 | −51.5 | −179.3 | −108.9 | −83.8 | D | 11.72 |
| GmGTAmG | 67.8 | −87.1 | 170.5 | 130.3 | −66.4 | D | 12.06 |
| GGTAG | 76.5 | 41.6 | 175.5 | 110.8 | 81.4 | D | 12.13 |
| GGTmAG | 73.2 | 46.3 | −175.1 | −125.4 | 66.5 | D | 12.13 |
| AmGmATT | 128.4 | −73.9 | −107.8 | 178.8 | 174.8 | C | 12.16 |
| GGATG | 48.1 | 36.8 | 100.5 | −177.1 | 49.5 | C | 12.19 |
| AGATmG | 119.4 | 46.3 | 130.3 | 171.2 | −56.7 | C | 12.30 |
| AGTmAG | 144.8 | 87.5 | −173.6 | −125.1 | 63.3 | D | 12.36 |
| GmAATG | 78.5 | −96.5 | 131.4 | 166.7 | 59.4 | C | 12.76 |
| AmGTmAmA | 147.0 | −42.0 | −179.6 | −110.1 | −149.8 | D | 12.89 |
| AAmATG | 144.7 | 90.6 | −133.2 | −168.4 | 58.0 | C | 13.28 |
| AmGTmAG | 145.9 | −38.8 | −171.3 | −125.8 | 66.8 | D | 14.00 |
| AAmATmG | 135.5 | 93.7 | −125.4 | −171.3 | −49.8 | C | 14.35 |
| TGmATT | 151.3 | 89.0 | −131.3 | −170.6 | −161.3 | C | 15.44 |
| TmAATT | 150.7 | −110.2 | 126.6 | 171.9 | −176.9 | C | 15.53 |
| GGAGG | 59.2 | 46.5 | 128.2 | 40.5 | 72.3 | E | 17.59 |
| GGGAG | 55.0 | 61.7 | 48.6 | 114.9 | 74.7 | F | 18.76 |
| GTGAG | 54.7 | 154.2 | 56.0 | 114.7 | 84.5 | G | 60.22 |

[a]E = −1075852.61 kcal/mol.

TABLE 13

Comparison of the *ab Initio* Relative Energies (kcal/mol) of Selected Magnesium 2-O-methyldiphosphono-tetrahydropyran (2) Conformers Calculated by Different Methods

| | Energy | Geometry | GmAGmAmG | GmAGTmG | GGmGTG | GmGmATG | GmGTmAmG |
|---|---|---|---|---|---|---|---|
| HF | 6-31G* | 6-31G* | 0.00 | 4.13 | 4.92 | 9.67 | 9.81 |
| HF | 6-31+FG** | 6-31G* | 0.00 | 5.00 | 5.75 | 9.48 | 9.97 |
| HF | 6-31++G** | 6-31++G** | 0.00 | 5.06 | 5.73 | 9.33 | 9.93 |
| DFT/B3LYP | 6-31G** | 6-31G** | 0.00 | 2.13 | 3.58 | 12.56 | 12.04 |
| DFT/B3LYP | 6-31++G** | 6-31G** | 0.00 | 3.67 | 4.17 | 11.62 | 11.38 |
| DFT/B3LYP | 6-31++G** | 6-31++G** | 0.00 | 3.55 | 4.08 | 11.21 | 11.38 |
| LMP2 | 6-31++G** | 6-31G** | 0.00 | 2.76 | 4.98 | 11.92 | 12.30 |
| LMP2 | 6-31++G** | 6-31++G** | 0.00 | 2.12 | 3.75 | 10.15 | 10.70 |

TABLE 14

Summary of Corrections to the Calculated Free Energy Differences (kcal/mol) for the Selected Magnesium 2-O-methyldiphosphono-tetrahydropyran (2) Conformers in Gas Phase, Cyclohexane and Water at 298K

| | Methods | GmAGmAmG | GmAGTmG | GGmGTG | GmGmATG | GmGTmAmG |
|---|---|---|---|---|---|---|
| ZPE | HF/6-31G* | 127.36 | 128.64 | 130.01 | 127.07 | 126.92 |
| $\Delta G_{vibrrot}$ | HF/6-31G* | −26.30 | −26.56 | −24.99 | −27.82 | −27.63 |
| $\Delta G(Cyclohexane)_{Solv}$ | B3LYP/6-31G** | −18.64 | −14.82 | −16.08 | −22.62 | −22.82 |
| $\Delta G(Water)_{Solv}$ | B3LYP/6-31G** | −63.59 | −48.80 | −59.80 | −76.24 | −66.84 |
| ΔE | HF/6-31++G** | 0.00 | 5.06 | 5.73 | 9.33 | 9.93 |
| $\Delta G_{gas}$ | | 0.00 | 4.57 | 8.03 | 9.58 | 9.59 |
| $\Delta G_{Cyclohexane}$ | | 0.00 | 8.39 | 10.59 | 5.40 | 5.41 |
| $\Delta G_{water}$ | | 3.28 | 22.63 | 15.10 | 0.00 | 9.62 |
| ΔE | B3LYP/6-31++G** | 0.00 | 3.55 | 4.08 | 11.21 | 11.38 |
| $\Delta G_{gas}$ | | 0.00 | 4.57 | 8.04 | 9.40 | 9.61 |
| $\Delta G_{cyclohexane}$ | | 0.00 | 8.40 | 10.60 | 5.42 | 5.43 |
| $\Delta G_{water}$ | | 3.26 | 22.62 | 15.08 | 0.00 | 9.62 |
| ΔE | LMP2//6-31++G** | 0.00 | 2.12 | 3.75 | 10.15 | 10.70 |
| $\Delta G_{gas}$ | | 0.00 | 3.14 | 7.71 | 8.34 | 8.93 |
| $\Delta G_{Cyclohexane}$ | | 0.00 | 6.96 | 10.27 | 4.36 | 4.75 |
| $\Delta G_{water}$ | | 4.31 | 22.24 | 15.81 | 0.00 | 10.00 |

TABLE 15

*Ab Initio* Relative Energy (kcal/mol), Binding Energy per One Water Molecule (kcal/mol), and the Position of the Magnesium 2-O-methyldiphosphono-tetrahydropyran (2) Conformers in Clusters with $N_{water}$ Water Molecules at the 6-31G* Level

| Starting Conformers | Cluster Conformation | φ | $\Psi_1$ | $\Psi_2$ | $\Psi_3$ | $\Psi_4$ | ΔE | BE[a] |
|---|---|---|---|---|---|---|---|---|
| Two water molecules ($N_{waters}$ = 2) | | | | | | | | |
| GGmGTG | GGmGTG | 52.5 | 62.4 | −93.1 | −177.1 | 58.9 | 0.00[b] | 30.6 |
| Three water molecules ($N_{waters}$ = 3) | | | | | | | | |
| GmAGmAmG, GmAGTmG | GmAGmAmG | 84.9 | −133.3 | 87.3 | −149.7 | −67.0 | 0.00[c] | 29.2 |
| GmGmATG | GmGmATG | 77.4 | −82.1 | −97.0 | 171.6 | 53.4 | 6.59 | 30.3 |
| GmGTmAmG | GmGTmAmG | 70.7 | −80.9 | 172.5 | −91.4 | −68.2 | 6.68 | 30.3 |
| ATATmG | AmAGTmG | 93.8 | −141.5 | 96.6 | −171.1 | −54.9 | 2.78 | 32.0 |
| Four water molecules ($N_{waters}$ = 4) | | | | | | | | |
| GGAGG | GGAGG | 57.7 | −80.5 | 171.8 | 68.6 | 66.4 | 0.00[d] | 30.0 |
| GGGAG | GGGAG | 172.5 | 107.1 | 60.9 | 113.4 | 76.6 | 3.20 | 29.5 |
| GTGAG | GTGAG | 57.1 | 174.9 | 70.8 | 97.8 | 80.9 | 33.26 | 32.4 |

[a]BE is a crude estimate of the binding energy for a single water calculated as BE = -[E(cluster) − E(2) − $N_{water}$E(water)]/$N_{water}$ with E(water) = −47697.56 kcal/mol,
[b]E = −1171303.99 kcal/mol,
[c]E = −1219032.65 kcal/mol,
[d]E = −1266745.00 kcal/mol.

TABLE 16

| Enzyme | Donor | Acceptor |
|---|---|---|
| α-1,3-mannosyl-glycoprotein β-1,2 N-acetylglucosaminyl transferase (GnT 1) (EC 2.4.1.101) | UDP-D-GlcNAc | α-D-mannosyl-1,3(R1)- β-D-mannosyl-R2 |
| α-1,6-mannosyl-glycoprotein-β 1,2 N-acetylglucosaminyl transferase (GAT) (GnT II) (EC 2.4.1.143) | UDP-D-GlcNAc | α-D-mannosyl-1,6(N-acetyl- β-D glucosaminyl-1,2-α-D- (mannosyl-1,3-)-β-D- mannosyl-R |
| α-1,3(6)-mannosylglycoprotein β 1,6-N-acetyl-glucosaminyl transferase (EC 2.4.1.155) (GnT V) | UDP-D-GlcNAc | N-acetyl-βD-glucosaminyl- 1,2 alpha-D-mannosyl- 1,3(6)-(N-acetyl-β-D- glucosaminyl-1,2-a-D-mannosyl- 1,6(3)-βD-mannosyl-1,4-N-acetyl-β- D-glucosaminyl-R |
| β-1,3-galactosyl-O-glycosyl glycoprotein-β1,6-N acetylglucosaminyl transferase (EC 2.4.1.102) (β1,6 (O-linked, core 2)) | UDP-D-GlcNAc | β-D-galactosyl-1,3 N- acetyl-D-galactosaminyl-R |
| β-1,4-mannosyl-glycoprotein β-1,4-N-acetylglucosaminyl transferase (GnT III) (EC 2.4.1.144) | UDP-D-GlcNAc | N-acetyl-βD-glucosaminyl-1,2 alpha-D-mannosyl-1,3-(N-acetyl- β-D-glucosaminyl-1,2-α-D- mannosyl-1,6)-β-D-mannosyl-1,4- N-acetyl-β-D-glucosaminyl-R |

We claim:

1. A computer-implemented method for designing potential inhibitors of a glycosyltransferases comprising:

A. designing a nucleotide-sugar with a monophosphate linkage by (a) selecting a molecule comprising a first sugar, a phosphate group, and a second sugar that is transferred by the glycosyltransferase to an acceptor for the glycosyltransferase, wherein there is a bond between a carbon atom of the first sugar and a first oxygen atom of the phosphate group, and a linkage between a carbon atom of the second sugar and a second oxygen atom of the phosphate group, (b) optimizing the orientation of the molecule using ab initio quantum chemistry methods so that the orientation of the linkage is antiperiplanar;

B. designing a nucleotide-sugar with a monophosphate linkage and having an electrostatic interaction between free oxygen atoms of the monophosphate and an ion by (a) selecting a molecule comprising a first sugar, a phosphate, and a second sugar that is transferred by the glycosyltransferase to an acceptor for the glycosyltransferase, wherein there is a bond between a carbon atom of the first sugar and a first oxygen atom of the phosphate group, a linkage between a carbon atom of the second sugar and a second oxygen atom of the phosphate group, and an electrostatic interaction between free oxygen atoms of the phosphate group and the ion, (b) optimizing the orientation of the molecule using ab initio quantum chemistry methods so that the orientation of the linkage is synclinal;

C. designing a nucleotide-sugar with a diphosphate linkage by (a) selecting a molecule comprising a first sugar, a diphosphate group, and a second sugar that is transferred by the glycosyltransferase to an acceptor for the glycosyltransferase, and wherein there is a bond between a carbon atom of the first sugar and an oxygen atom of a first phosphate of the diphosphate group, and a linkage between a carbon atom of the second sugar and an oxygen atom of a second phosphate of the diphosphate group, and (b) optimizing the conformation of the molecule using ab initio quantum chemistry methods so that the orientation of the linkage is antiperiplanar, and phosphorous-oxygen bonds linking the first phosphate to the second phosphate of the diphosphate group are in a synclinal or anticlinal orientation, and synclinal orientation, respectively, or symmetrically related orientations; or D. designing a nucleotide-sugar with a diphosphate linkage and having an electrostatic interaction between free oxygen atoms of the diphosphate and the ion by (a) selecting a molecule comprising a first sugar, a diphosphate group, an ion, and a second sugar that is transferred by the glycosyltransferase to an acceptor for the glycosyltransferase, wherein there is a bond between a carbon atom of the first sugar and an oxygen atom of a first phosphate of the diphosphate group, a linkage between a carbon atom of the second sugar and an oxygen atom of a second phosphate of the diphosphate group, and an electrostatic interaction between two or more free oxygen atoms of the diphosphate group and the ion, (b) optimizing the conformation of the molecule using ab initio quantum chemistry methods so that the orientation of the linkage is synclinal, phosphorous-oxygen bonds linking the first phosphate to the second phosphate of the diphosphate group are in antiperiplanar or -anticlinal orientation, and synclinal orientation, respectively, or symmetrically related orientations.

2. A computer-implemented method for designing a potential inhibitor of a glycosyltransferase comprising (a) selecting a molecule comprising a group of the formula I

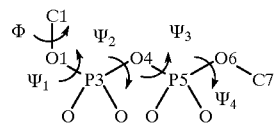

wherein C7 forms part of a first sugar; C1 forms part of a second sugar that is transferred by the glycosyltransferase to an acceptor for the glycosyltransferase; $\Phi$ is a dihedral angle defining rotation about C1—O1; $\Psi_1$ is a dihedral angle defining orientation about O1—P3; $\Psi_2$ is a dihedral angle defining orientation about P3—O4, $\Psi_3$ is a dihedral angle defining orientation about O4—P5, and (b) optimizing the conformation of the molecule so that $\Phi$ is in an antiperiplanar orientation, $\Psi_2$ is in a synclinal orientation or symmetrically related orientation, and $\Psi_3$ is in a synclinal or anticlinal orientation or a symmetrically related orientation.

3. A computer-implemented method for designing a potential inhibitor of a glycosyltransferase comprising (a) selecting a molecule comprising a group of the formula I and an ion

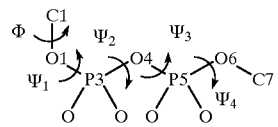

wherein C7 forms part of a first sugar; C1 forms part of a second sugar that is transferred by the glycosyltransferase to an acceptor for the glycosyltransferase; $\Phi$ is a dihedral angle defining rotation about C1—O1; $\Psi_1$ is a dihedral angle defining orientation about O1—P3; $\Psi_2$ is a dihedral angle defining orientation about P3—O4, and $\Psi_3$ is a dihedral angle defining orientation about O4—P5, and (b) optimizing the conformation of the molecule so that there is an electrostatic interaction between two or more free oxygen atoms of the molecule of the formula I and the ion, $\Phi$ is in a synclinal orientation, $\Psi_2$ is in a synclinal or a symmetrically related orientation, $\Psi_3$ is in an -anticlinal or antiperiplanar orientation or a symmetrically related orientation.

4. A computer-implemented method as claimed in claim 1 wherein the glycosyltransferase inhibitor is an inhibitor of a eukaryotic glycosyltransferase involved in the biosynthesis of glycoproteins, glycolipids, glycosylphosphatidylinositols or other complex glycoconjugates, or a prokaryotic glycosyltransferase involved in the synthesis of carbohydrate structures of bacteria and viruses.

5. A computer-implemented method as claimed in claim 1 wherein the first sugar is a monosaccharide or disaccharide.

6. A computer-implemented method as claimed in claim 1 wherein the first sugar is ribose or deoxyribose.

7. A computer-implemented method as claimed in claim 1 wherein the first sugar is part of a nucleoside.

8. A computer-implemented method as claimed in claim 1 wherein the first sugar is part of uridine.

9. A computer-implemented method as claimed in claim 1 wherein the second sugar is D—GlcNAc.

10. A computer-implemented method as claimed in claim 1, paragraph D, wherein the ion is sodium, lithium, potassium, calcium, magnesium, manganese, a cobalt ion, ammonium, tetramethylammonium, tetraethylammonium, methylamine, dimethylamine, trimethylamine, triethylamine, or ethylamine.

11. A computer-implemented method as claimed in claim 2 wherein $\Phi$ is between about 100° and 170° or symmetrically related orientations, $\Psi_2$ is between about 60° and 120° or symmetrically related orientations, and $\Psi_3$ is between about −50° and −130°, or symmetrically related orientations.

12. A computer-implemented method as claimed in claim 3 wherein $\Phi$ is between about 100° and 170° or symmetrically related orientations, $\Psi_2$ is between about 60° and 120° or symmetrically related orientations, and $\Psi_3$ is between about −50° and −130°, or symmetrically related orientations.

13. A computer-implemented method as claimed in claim 2 wherein $\Psi_2$ is in a synclinal orientation and $\Psi_3$ is in an -anticlinal orientation.

14. A computer-implemented method as claimed in claim 3 wherein $\Psi_2$ is in a synclinal orientation and $\Psi_3$ is in an -anticlinal orientation.

15. A computer-implemented method as claimed in claim 2 wherein $\Phi$ is between about 40° and 100° or symmetrically related orientations, $\Psi_2$ is between about 60° and 110° or symmetrically related orientations, and $\Psi_3$ is between about −90° and −100° (-ac) or 180±10° (ap) or symmetrically related orientations.

16. A computer-implemented method as claimed in claim, 3 wherein $\Phi$ is between about 40° and 100° or symmetrically related orientations, $\Psi_2$ is between about 60° and 110° or symmetrically related orientations, and $\Psi_3$ is between about −90° and −100° (-ac) or 180±10° (ap) or symmetrically related orientations.

* * * * *